(12) United States Patent
Jiao et al.

(10) Patent No.: US 11,380,423 B2
(45) Date of Patent: **\*Jul. 5, 2022**

(54) COMPUTING SYSTEM IMPLEMENTING A HEALTH SERVICE FOR CORRELATING HEALTH KNOWLEDGE AND ACTIVITY DATA WITH PREDICTIVE HEALTH OUTCOMES

(71) Applicant: Hi.Q, Inc., Mountain View, CA (US)

(72) Inventors: Shuo Jiao, Sunnyvale, CA (US);
Munjal Shah, Los Altos, CA (US);
Ardaman Singh, Union City, CA (US)

(73) Assignee: Hi.Q, Inc., Mountain View, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 16/783,989

(22) Filed: Feb. 6, 2020

(65) Prior Publication Data
US 2020/0251189 A1    Aug. 6, 2020

Related U.S. Application Data

(63) Continuation of application No. 14/642,709, filed on Mar. 9, 2015, now Pat. No. 10,629,293, which is a
(Continued)

(51) Int. Cl.
*G16H 10/20* (2018.01)
*G16H 50/30* (2018.01)

(52) U.S. Cl.
CPC .............. *G16H 10/20* (2018.01); *G16H 50/30* (2018.01)

(58) Field of Classification Search
CPC ................................ G16H 10/20; G16H 50/30
(Continued)

(56) References Cited

U.S. PATENT DOCUMENTS 5,572,421 A    11/1996  Altman et al.
5,639,471 A    6/1997   Chait
(Continued)

FOREIGN PATENT DOCUMENTS

CA        2887411     10/2015
CN      105760692 A    7/2016
(Continued)

OTHER PUBLICATIONS

Kwak, Jang Yul; Determinants of users' intention to adopt mobile fitness applications: An extended technology acceptance model approach; The University of New Mexico. ProQuest Dissertations Publishing, 2014. 3641225. (Year: 2014).*

(Continued)

*Primary Examiner* — Hiep V Nguyen
(74) *Attorney, Agent, or Firm* — Mahamedi IP Law LLP

(57) ABSTRACT

A computing system includes a database having a collection of health-related assertions for a health quiz to be taken by users. Each health assertion is tuned with a correlative health value based on answers to the health assertion provided by a control group of users. For each user in the control group, at least one health outcome is known, and therefore the computing system can use a big data approach to determine the correlative value for each health assertion to the actual health outcomes of the control group users. Using the correlative values for each health assertion, the computing system can generate a health profile of each user who takes the health quiz. In certain examples, the health quiz correlation can be combined with activity monitoring data to develop a highly accurate health profile for each user.

20 Claims, 12 Drawing Sheets

Related U.S. Application Data continuation-in-part of application No. 14/542,347, filed on Nov. 14, 2014, now Pat. No. 10,672,519.

(58) Field of Classification Search
USPC .............................................................. 705/2
See application file for complete search history.

(56) References Cited

U.S. PATENT DOCUMENTS

| | | | |
|---|---|---|---|
| 5,711,297 A * | 1/1998 | Iliff | G16H 10/60 |
| | | | 600/300 |
| 5,879,163 A | 3/1999 | Brown | |
| 6,151,581 A | 11/2000 | Kraftson | |
| 7,319,970 B1 | 1/2008 | Simone | |
| 9,727,885 B1 | 8/2017 | Reier | |
| 10,878,062 B1 | 12/2020 | Garavaglia et al. | |
| 2002/0035486 A1 | 3/2002 | Huyn et al. | |
| 2003/0027122 A1 | 2/2003 | Stansvik | |
| 2003/0195772 A1 | 10/2003 | Meek | |
| 2005/0102171 A1 | 5/2005 | Ashley | |
| 2005/0182659 A1 | 8/2005 | Huttin | |
| 2005/0228692 A1 | 10/2005 | Hodgdon | |
| 2005/0234742 A1 | 10/2005 | Hodgdon | |
| 2007/0061166 A1 | 3/2007 | Ramasubramanian | |
| 2007/0118398 A1 | 5/2007 | Peris | |
| 2007/0129611 A1 | 6/2007 | Ratka | |
| 2008/0147441 A1 | 6/2008 | Kil | |
| 2009/0055915 A1 | 2/2009 | Piliouras | |
| 2009/0111085 A1 | 4/2009 | Rudy | |
| 2009/0241028 A1 | 9/2009 | Iskedjian | |
| 2010/0004947 A1 | 1/2010 | Nadeau | |
| 2011/0022420 A1 | 1/2011 | Morse | |
| 2011/0046985 A1 | 2/2011 | Raheman | |
| 2011/0307311 A1 * | 12/2011 | Turgiss | G16H 40/67 |
| | | | 705/14.4 |
| 2012/0004925 A1 | 1/2012 | Braverman | |
| 2012/0041788 A1 | 2/2012 | Wons | |
| 2012/0123802 A1 | 5/2012 | Feldman | |
| 2012/0156664 A1 | 6/2012 | Hurwitz | |
| 2012/0251993 A1 | 10/2012 | Chidambaran et al. | |
| 2013/0024212 A1 * | 1/2013 | Atakhorrami | G16H 10/20 |
| | | | 705/3 |
| 2013/0035207 A1 | 2/2013 | Abuelsaad | |
| 2013/0096942 A1 | 4/2013 | Bowles | |
| 2013/0117040 A1 | 5/2013 | James et al. | |
| 2013/0138450 A1 | 5/2013 | Vigneux | |
| 2013/0211858 A1 | 8/2013 | Ohnemus | |
| 2013/0230841 A1 | 9/2013 | Bremer | |
| 2013/0291098 A1 | 10/2013 | Chung | |
| 2013/0332189 A1 | 12/2013 | Manning | |
| 2014/0087355 A1 | 3/2014 | Henry | |
| 2014/0156308 A1 | 6/2014 | Ohnemus | |
| 2014/0214441 A1 | 7/2014 | Young | |
| 2014/0257852 A1 | 9/2014 | Walker | |
| 2014/0278474 A1 * | 9/2014 | McClure | G16H 40/67 |
| | | | 705/2 |
| 2014/0316811 A1 | 10/2014 | Ohnemus | |
| 2014/0372133 A1 | 12/2014 | Austrum | |
| 2015/0019266 A1 | 1/2015 | Stempora | |
| 2015/0046174 A1 | 2/2015 | Mainwaring | |
| 2015/0104759 A1 | 4/2015 | Block | |
| 2015/0161538 A1 | 6/2015 | Matus | |
| 2015/0161738 A1 | 6/2015 | Stempora | |
| 2015/0178920 A1 | 6/2015 | Garnavi et al. | |
| 2015/0317650 A1 | 11/2015 | Mahoney | |
| 2016/0049084 A1 | 2/2016 | Chamberlain | |
| 2016/0086505 A1 | 3/2016 | Hanlon | |
| 2016/0140310 A1 | 5/2016 | Jiao et al. | |
| 2016/0140323 A1 | 5/2016 | Jiao et al. | |
| 2016/0140642 A1 | 5/2016 | Jiao et al. | |
| 2016/0140859 A1 | 5/2016 | Jiao et al. | |
| 2016/0188813 A1 | 6/2016 | Hennenfent | |
| 2016/0203284 A1 | 7/2016 | Ouyan | |
| 2016/0246947 A1 | 8/2016 | Yao | |
| 2016/0335404 A1 | 11/2016 | Srinivas | |
| 2017/0103179 A1 | 4/2017 | Jiao et al. | |
| 2017/0103180 A1 | 4/2017 | Jiao et al. | |
| 2017/0103469 A1 | 4/2017 | Jiao et al. | |
| 2017/0109829 A1 | 4/2017 | Amigo | |
| 2017/0132396 A1 | 5/2017 | Bechtold | |
| 2017/0193165 A1 | 7/2017 | Mandalika | |
| 2018/0144829 A1 | 5/2018 | Cantor | |
| 2019/0026364 A1 | 1/2019 | Sankovsky | |
| 2019/0095590 A1 | 3/2019 | Knoop | |
| 2019/0139146 A1 | 5/2019 | Sato et al. | |
| 2019/0180852 A1 | 6/2019 | Jiao et al. | |
| 2020/0251221 A1 | 8/2020 | Jiao et al. | |
| 2020/0251222 A1 | 8/2020 | Jiao et al. | |
| 2021/0082056 A1 | 3/2021 | Hirobe | |
| 2021/0192454 A1 | 6/2021 | Jiao et al. | |
| 2021/0210176 A1 | 7/2021 | Jiao et al. | |

FOREIGN PATENT DOCUMENTS

| | | | |
|---|---|---|---|
| CN | 108734592 | 11/2018 | |
| JP | 2002123612 | 4/2002 | |
| JP | 2013524332 | 6/2013 | |
| KR | 10-2016-0050573 A | 5/2016 | |
| SG | 10201902514 W | 8/2020 | |
| WO | WO-2011/058463 A2 | 5/2011 | |
| WO | WO-2016/050990 A1 | 4/2016 | |
| WO | WO-2016/077781 | 5/2016 | |
| WO | WO-2016077781 A1 * | 5/2016 | ......... G06Q 30/0631 |
| WO | WO-2018/057798 | 3/2018 | |
| WO | WO-2019/202707 | 10/2019 | |

OTHER PUBLICATIONS

International Search Report and Written Opinion from PCT Application No. PCT/US2015/060723, dated Feb. 4, 2016, 9 pages.
Notification Concerning Transmittal of International Preliminary Report on Patentability PCT Application No. PCT/US2015/060723, dated May 26, 2017, 8 pages.
International Search Report and Written Opinion from PCT Application No. PCT/US2017/052804, dated Dec. 7, 2017, 7 pages.
Prokoshfna N.R. Prognozirovanie otnositelnogo riska obschey smertnosti u lits s arterialnoy gipertenziey (po dannym desyatiletnego kogortnogo issledovaniya).Vestnik Vitebskogo gosudarstvennogo meditsinskogo universiteta, 2011, pp. 54-62 Abstract in English.
Batura T.V. Programmnye produkty i sistemy. Nauchno-Prakticheskoe izdanie. Tver 2013, X2 3 (103), pp. 130-137 Abstract in English.
European Search Report dated Jul. 23, 2018, Application No. 15859764.1 8 pages.
Office Action dated Oct. 1, 2019, Japanese Application No. 2017-526588, 12 pages.
Karen B. DeSalvo et al., Mortality Prediction with a Single General Self-Rated Health Question, Journal of General Internal Medicine 21:3, pp. 267-275 (Mar. 2006), https://onlinelibrary.wiley.com/doi/full/10.111/j.1525-1497.2005.00291.x (last visited on Sep. 25, 2019) (Year:2006).
European Examination Report dated Dec. 11, 2019, Application No. 15859764.1 11 pages.
European Search Report dated Feb. 11, 2020, Application No. 17853933.4 11 pages.
Office Action dated Jun. 9, 2020, Japanese Application No. 2017-526588, 6 pages.
Australian Examination Report dated Jul. 28, 2020, Application No. 2015346070 3 pages.
International Search Report and Written Opinion from PCT Application No. PCT/US2021/038287, dated Sep. 15, 2021, 10 pages.
International Search Report and Written Opinion from PCT Application No. PCT/US2021/054178, dated Jan. 13, 2022, 13 pages.
Australian Examination Report dated Jan. 12, 2022, Application No. 2017331252 4 pages.

* cited by examiner

| QID | HO1 | HO2 | HO3 | HO4 | Topic1 | Topic2 | Topicn |
|---|---|---|---|---|---|---|---|
| 0001 | CF1 | 0 | 0 | 0 | TCF1 | TCF2 | 0 |
| 0002 | 0 | CF2 | 0 | 0 | 0 | TCF4 | |
| 0003 | 0 | 0 | 0 | CF4 | 0 | 0 | TCF5 |
| 0004 | 0 | 0 | CF3 | 0 | 0 | 0 | |
| 0005 | 0 | 0 | 0 | 0 | 0 | 0 | |
| 0006 | 0 | 0 | 0 | 0 | 0 | 0 | |

COMPUTING SYSTEM IMPLEMENTING A HEALTH SERVICE FOR CORRELATING HEALTH KNOWLEDGE AND ACTIVITY DATA WITH PREDICTIVE HEALTH OUTCOMES

CROSS-REFERENCE TO RELATED APPLICATIONS

This application is a continuation of U.S. patent application Ser. No. 14/642,709, filed on Mar. 9, 2015; which is a continuation-in-part of U.S. patent application Ser. No. 14/542,347, filed Nov. 14, 2014; the aforementioned applications being hereby incorporated by reference in their respective entireties.

TECHNICAL FIELD

Examples described herein relate to a system and method for providing a health determination service based on user knowledge and activity.

BACKGROUND

Online services exist which provide interactive gaming and social environments for users. These services generally exist for amusement only.

There also exists a questionnaire, termed the Patient Activation Measure ("PAM"), provided by Insignia Health under license from the State of Oregon, which includes a static set of questions that are knowledge-based and deemed correlative to health.

DETAILED DESCRIPTION

Figure 1:
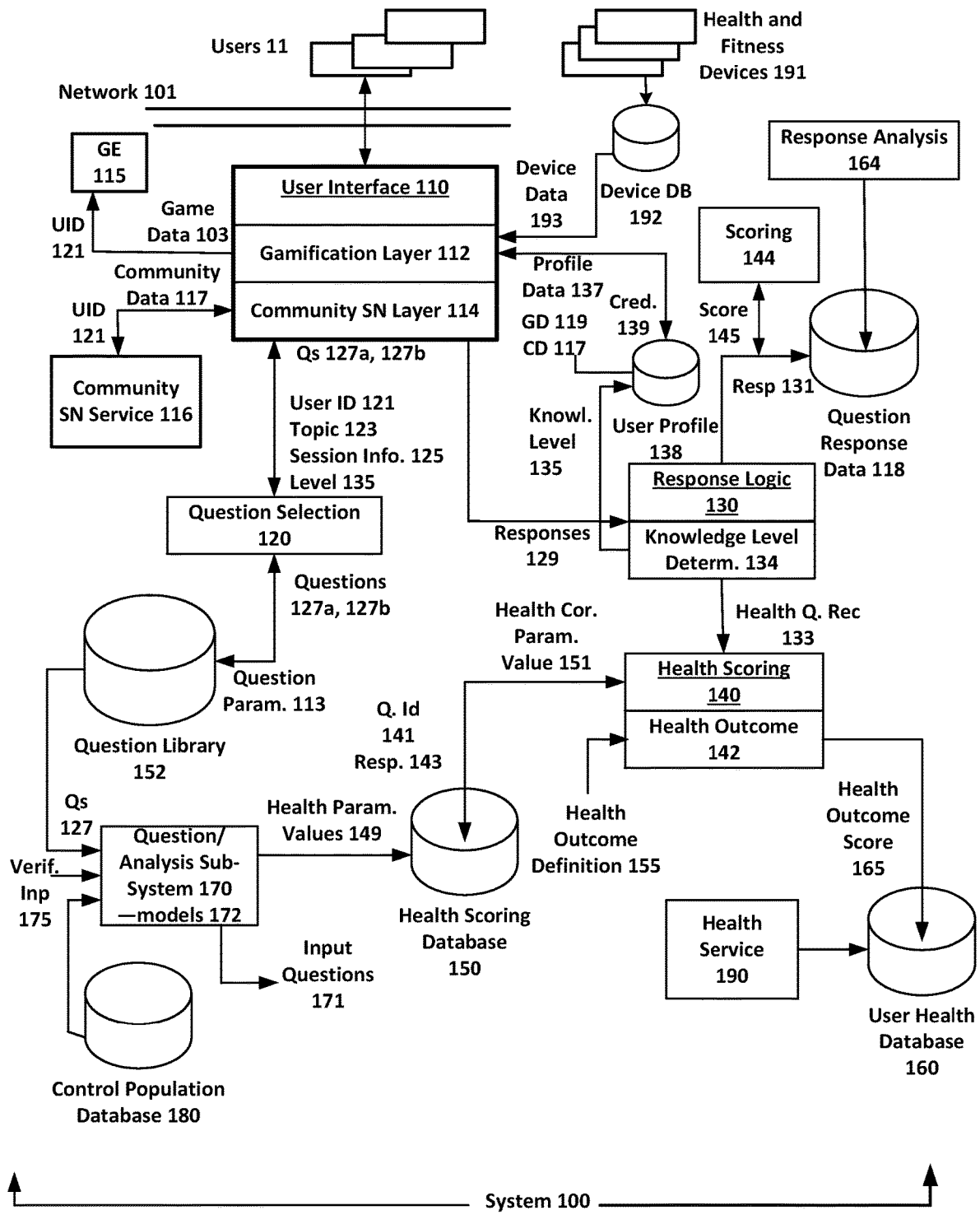
FIG. 1 illustrates a system for predicting a physiological or mental health of a user based on the user's knowledge level of health, according to one or more embodiments.

Some embodiments include a system and method for predicting a health outcome of a user based on a determination of knowledge the user possesses regarding issues of physiological or mental health.

Still further, in some embodiments, a system and method are provided for providing a health service benefit to a user based on the user's predicted health, as determined from the user's knowledge of human health.

In one embodiment, a collection of assertions are stored in which each assertion pertains to human health. For each individual in a control population of persons, a value of a predetermined health parameter is determined which is indicative of that person's health. For each assertion of the collection, a correlative health parameter is determined which is indicative of an association between those individuals in the control population that have independent knowledge of the assertion and the value of the predetermined health parameter for persons of the control population. The collection of assertions can be stored by associating each assertion with the determined correlative health parameter for that assertion. An interface is provided for a user to indicate the user's independent knowledge of each assertion in at least a subset of assertions from the collection. A health outcome is predicted for the user based at least in part on the correlative health parameter of individual assertions in the subset of assertions.

In still another embodiment, a health outcome of a user is predicted based on a knowledge profile determination of the user. In one embodiment, a knowledge profile is determined for the user which reflects the user's independent knowledge of individual assertions in a collection of assertions. A correlation is determined as between a set of facets of the user's knowledge profile and a corresponding set of facets of multiple individual person's knowledge profile. The knowledge profile can be determined for at least a set of assertions from the collection of assertions. A health outcome is determined for each of the multiple individual persons. The health outcome of the user can then be predicted based in part on the correlation and the health outcome of each of the multiple individuals.

In still another embodiment, a knowledge profile is determined for the user to reflect the user's independent knowledge of individual assertions in a collection of assertions. Each assertion in the collection can be non-specific to the user or to any person of the population, but otherwise known to be correlative to human health. A determination is made as to a first correlation value as between the knowledge profile of the user and a knowledge profile of a control group of persons for whom one or more health outcomes are known. A first health outcome is predicted for the user based on the first correlation value. A health service benefit is provided to the user based at least in part on the predicted health outcome.

Still further, according to another embodiment, a human health knowledge profile is determined for each user in a group of users, the human health knowledge profile reflecting that user's independent knowledge about assertions in a collection of assertions. Each assertion in the collection of assertions may pertain to human health and is non-specific as to any user or to any person of the population. At least a first correlation value is determined as between a facet of the knowledge profile of individual users in the group of users and a corresponding facet of the knowledge profile of a control group of persons for whom one or more health outcomes are known. A subset of one or more users is selected based on the first correlation value of each user of the subset exceeding a threshold designation. A service or designation is provided for a set value to the one or more users of the subset, and not to other users of the group. The service or designation may be associated with a true per-user cost that is not equal to the set value, but which is variable and set to increases over time when individual users in the subset suffer negative health consequences as a result of a naturally progressing medical condition. Still further, some embodiments include a system and method for providing a health service or benefit to a user. By way of example, a health service or benefit can include health insurance (including primary or supplemental), life insurance, enrollment in a facility to receive medical attention, medical publications, as well as discounts or augmented services thereof. In one embodiment, a collection of questions are stored, where each question is based on a documented assertion pertaining to human health. Each question in a first subset may be associated with a correlative health parameter that is based at least in part on (i) persons in a control population of that have independent knowledge of an assertion that is a basis of that question, and (ii) a value of a predetermined health parameter for each person in the control population the value of the predetermined health parameter for each person being indicative of that person's health. Additionally, the second subset of the questions is associated with a null (i.e. non-existent) or neutral (i.e., not indicative of health) correlative health parameter. A corresponding set of questions is displayed to the user from the collection for response for each user in the set of users. A response score is determined for each user in the set of users based on a correctness of their respective reply to each question in the corresponding set of questions. A health parameter value is determined for at least a health outcome based at least in part on the correlative health parameter of at least some questions in the corresponding set of questions.

Still further, some embodiments include a system and method for providing health recommendations to a user. In an embodiment, a plurality of questions are provided to the user. The plurality of questions can include multiple questions for each of multiple health-related topics, so that individual questions are each associated with one or more of the multiple topics. A score is determined for the user in answering each question in the plurality of questions. The score can include topical scores for one or more of the multiple topics. Based on the topical score of at least a first topic, a set of recommendations can be identified for the user. The set of recommendations may include an action that the user can perform to improve the user's mental or physiological health relating to the topic.

According to some embodiments, contextual data is determined from user activity, and more specifically, from health-related activity recorded by a user device. The user device can correspond to, for example, a mobile device that the user can carry on their person (e.g., mobile device in arm holster), or by a wearable electronic device. By way of example, a wearable electronic device can include computerized devices that record movement, location, and/or a user's biometric output (e.g., temperature or heartbeat). Wearable electronic devices can have a variety of form factors, such as, for example, a bracelet, watch, arm band, glassware, hat, or garment. Depending on design or implementation, such devices can operate independently or in communication with another computing device (e.g., via Bluetooth or wireless connection to another mobile computing device).

As used herein, an activity monitoring device includes any electronic device which the user can carry, such as a mobile computing device or wearable electronic device, which tracks and records user activity in the context of health. The recorded activity can include data relating to user exercise, as well as data relating to everyday activities such as sleeping, walking, eating, or working (e.g., sitting at desk). According to some embodiments, data generated by one or more activity monitoring devices is retrieved, and questions displayed to the user are based on this retrieved data.

While examples such as described are implemented on computer systems, empirical data has been derived to show health outcome prediction can be correlated to user's knowledge. For example, examples have determined that positive health outcome determinations made from evaluating user's answers directly correlate to fewer hospital stays.

System Overview

FIG. 1 illustrates a system for predicting a physiological or mental health of a user based on the user's knowledge level of health, according to one or more embodiments. A system 100 as shown by an example of FIG. 1 can be implemented using a combination of servers, or other computers which combine to provide a network service for client computers operated by a user base. While an example of FIG. 1 illustrates the system 100 being implemented as a combination of logical components, alternative implementations can readily provide for functionality described to be integrated or discrete. Moreover, specific combinations of functionality and processes described can alternatively be performed as sub-combinations or alternative combinations. Likewise, an example of FIG. 1 illustrates use of multiple data stores, which can logically and/or physically be implemented as a combined or integrated data structure (e.g., database), or alternatively, in distributed fashion such as shown.

Among other implementations, system 100 can be accessible to users 11 over a network 101, such as the World Wide Web, to mobile computing devices (e.g., feature phones, tablets, etc.), personal computers (e.g., desktop computers, laptops, etc.) and other user operated computing devices for purpose of interactively engaging individual users to determine their knowledge level on various health topics, and further for predicting the individual user's physiological or mental health based on their knowledge level of health. Among other advantages, an example of FIG. 1 enables facets of physiological or mental health to be determined for a person, without need for obtaining user specific medical information or biological samples. For example, in one implementation, a user's health can be predicted without use of any user-specific medical question. In a variation, a user's health can be predicted based only on inputs of gender and age. In another variation, data collected through activity monitoring devices can be used, alone or in combination with other inputs, to predict a user's health.

As described in greater detail, system 100 generates fact-based questions on various topics of health for purpose of (i) obtaining responses from users, and (ii) correlating some of those responses to physiological or mental health determinations. One of the underlying assumptions of system 100 is that the living habits and behaviors of people generally tends to have a measurable impact on their physiological or mental health, particularly when the assumption is applied to a statistically significant sample of people (e.g., hundreds or thousands of persons). Under a statistically significant sample, embodiments described herein have recognized that a correlation can be made as between the knowledge or awareness of individuals and their relative health outcome. More generally, embodiments recognize that health-conscious individuals are generally more knowledgeable about health and also more healthy as compared to less healthy people (e.g., individuals who suffer from obesity, heart disease, etc.). In fact, embodiments recognize that healthy individuals are significantly more conscientious of maintaining healthy living habits and activities, and with this mindset, such individuals are far more knowledgeable about health than the rest of the population.

With this recognition, embodiments described herein provide a system for gauging how conscientious a given user is with respect to health, based on the user's awareness of information that is specific and health driven embodiments further recognize that such. Such information, which in many cases may qualify as trivia, nevertheless provides a mechanism for delineating those individuals in the population who are in fact conscientious about healthy living habits. Furthermore, embodiments described herein programmatically correlate knowledge of health to physiologic health of individuals amongst a statistically significant sample size of users.

In order to gauge knowledge, an embodiment of FIG. 1 maintains a library of fact-based assertions on various subjects of human health, such as nutrition, exercise, medicine, etc. In an example of FIG. 1, the assertions are presented to users in the form of questions, for which responses can provide answers that are either correct or incorrect, and further enable evaluation of knowledge based on whether correct or incorrect answers were given by the users. While examples provide for assertions to be presented to users in the form of questions for purpose of validating their knowledge, other embodiments may use alternative forms of interaction in order to gauge the user's awareness or knowledge of a particular assertion. For example, the user may be provided a statement that is presented as an answer, and the interaction required of the user can be for the user to generate a question that yields the particular answer. In this reverse format, the user's ability to generate the question, combined with a statement as the presented answer, serves as a mechanism for determining whether the user has independent knowledge of the underlying assertion from which the statement was originally presented.

Still further, as described in greater detail, some embodiments utilize a collection of assertions, of which only some have been determined to correlate to physiological or mental health. The user may have no knowledge of which questions correlate to health, or that only some questions have direct correlation to health while others are being provided for alternative purposes (e.g. amusement). In some cases, the user may even have no knowledge that some of the assertions for which the user is responding to have any correlation to do with their actual physiological or mental health. Among other benefits, the use of many questions, in combination with questions that have been determined to correlate to physiological or mental health, preclude some individuals from 'gaming' the questions in a manner that masks their true knowledge level and awareness.

In more detail, system 100 includes a user interface 110, question selection logic 120, response logic 130, and health scoring logic 140. The question selection 120 can receive or access questions 127 from a question library 152, and the user interface 110 can present content based on the selected questions 127 to individual users in any one of a variety of computing environments that stimulate the individual to provide purposeful responses that reflect the user's understanding and knowledge for a topic of the question. The questions 127 can vary in their purpose. In one example, question library 152 includes (i) a first set of questions 127a which have been correlated to physiological or mental health, and (ii) a second set of questions 127b which have not been correlated to physiological or mental health, but which may serve the alternative purpose of providing trivia, factual information, and/or entertainment. Additionally, the questions of library 152 can be assigned to topics and sub-topics. Still further, the questions of the library 152 can be associated with a difficulty score, based on, for example, a correction rate amongst a control group of persons who answered the question.

When the user initiates a session, the user interface 110 may record a user ID 121 and session information 125. In implementation, the user interface 110 can authenticate the user, and provide credentials 139 for a user profile store 138 in order to obtain profile data 137. The profile data 137 can identify, for example, any one or more of (i) the topic that the user was previously being questioned on, (ii) a topic the user is interested in, (iii) identifiers to questions that the user as previously answered, and/or (iv) a determined knowledge level 135 of the user. With the profile data 137, the user interface 110 can identify parameters or other information for facilitating question selections for the user. In one example, the user interface 110 can use the profile information 137 to specify one or more topical parameters 123 and/or the knowledge level 135 of the user. In turn, the question selection 120 can select questions 127 based on parameters 113, which can be based on, for example, topic parameter 123, knowledge level 135, or user interest and/or preferences.

The profile data 137 can also include user-specific game data 119 (e.g., user's personalizations for gaming, historical performance on games, current game play state, etc.). Additionally, the profile data 137 can include the user's community or social network data 117 (user's personalizations for community or social network application, social network content, etc.). The user-specific game data 119 and community or social network data 117 can, for example, be loaded through the respective functional layers of the user interface 110 when the user initiates a session with a service of system 100.

In addition to using profile data 137 to create parameters 113, system 100 can also use device data 193, which can include indicators of a user's overall health and fitness levels, generated by activity monitoring devices 191 for parameters 113, alone or in combination with profile data 137. Activity monitoring devices 191 include electronic devices (e.g., wearable electronic devices) that can be worn or held by users 11 in order to track data related to the users' activity levels and health parameters.

An activity monitoring device 191 can include resources such as Global Positioning System (GPS), motion sensors, and/or sensors (e.g., heartbeat monitor) to record and track user activity, as well as biometric information of the user in performing such activity. Additionally, the activity monitoring device 191 can include sensors such as an accelerometer or accelerometer set, a gyroscope, a magnetometer, an ambient light sensor, heart rate sensor, temperature sensor and/or other sensors to measure facets of the user's body in performing an activity. The activity monitoring device 191 records activity data 193, which can include statistics like pace, distance, elevation, route history, heartbeat, body temperature and/or other information relating to the user activity. The activity data 193 can include both (i) raw or measured data and (ii) derived or computed data based on measured or raw data and/or user input. Additional examples of device data 193 include heart rate and heart rate trends, steps, distance traveled, floors climbed, calories burned (e.g., derived from distance, pace, and user weight/gender), active minutes, sleep quality, blood sugar, and cholesterol levels, among others.

In some aspects, activity monitoring devices 191 can store their data in a device database 192, which can be managed by a computing platform (e.g., APPLE HEALTHKIT, manufactured by APPLE INC.). Such computing platforms can allow for designated mobile applications to read and write data to the device database 192 based on a set of permissions. For example, the permissions allow a user to choose which applications have access to device data 193 in order to protect privacy and prevent unauthorized access to potentially sensitive information. In some implementations, system 100 may only use device data 193 if a user has specifically opted-in and given permission for the data to be accessed by the system.

The user interface 110 can be used to record responses 129 from individual users. In one implementation, each question 127 can be communicated to the user interface using a sequence in which the answer to the question is also packaged and presented to the user. Some conditional logic may also be provided with the question 127, so that, for example, if the user response is correct, the user is instantly notified and the next question is presented to the user. However, the conditional logic may render an alternative content in response to incorrect user response, specifically a panel or other information item which provides information regarding the actual answer to the question presented. In this way, the user is made more knowledgeable.

The responses 129 can correspond to input that identifies, for example, the user's answer to a particular question. The responses 129 can identify the answer of the user, the question that was answered, and an identifier of the user. In some implementations, each question 127 can further be associated with one or more subject matter topics. Response logic 130 can process the responses 129 from the various users. In one implementation, an initial determination of response logic 130 is whether the question identified with response 129 is pre-associated with a physiological or mental health correlation, or whether no such pre-association physiological or mental health correlation exists for the question. In one implementation, the response logic 130 records a corresponding response entry 131 for each response, regardless of whether the question of the response has pre-association with physiological or mental health. The response entry 131 can reflect whether the answer to the question is correct, as well as the true answer. In some implementations, the response entry 131 further links the question answered to topical designations for the question, as well as calibration or difficulty scoring.

Scoring logic 144 can process the answer of response entry 131 to determine a score value 145 to associate with the particular record entry. The score value 145 can be based in part on the difficulty level of the question, which in some implementations, is provided as a calibration coefficient that is pre-associated with the question. Thus, the mathematical process to tabulate scoring can include factors such as the number of questions the user correctly answered, the number of questions the user incorrectly answered, the difficulty parameter associated with each question, and/or secondary considerations such as the time it took for the user to provide the response and/or whether the user correctly answered the question on the first try. The score value 145 can be stored with the response data store 118.

Additionally, scoring logic 144 can also tally one or more aggregate or overall scores for the user based on a historical record of responses. For example, the response data store 118 can maintain one or more aggregate or ongoing subject matter topical scores (e.g., weight-lifting), as well as an overall score for the user. As described with other examples, scoring logic 144 can be used to develop comparative scoring as between users, based on their overall knowledge, session performance, and/or topical subject matter knowledge.

The response logic 130 can optionally include a knowledge level determination component 134. The knowledge level determination component 134 can determine from the response 129 the knowledge level 135 of the user. Alternatively, the knowledge determination component 134 can determine the knowledge level of the user from the difficulty parameter associated with the question and/or with the score output, as provided by the scoring component 144. The knowledge level determination component 134 can determine an overall knowledge level or a topic-specific knowledge level 135. The determined knowledge level(s) 135 can be stored as part of the user profile 138, so that the knowledge level of the user is communicated to the questions selection logic 120 when the user initiates a session with system 100.

For those selected questions which are identified as having a pre-associated physiological or mental health correlation, the response logic 130 can provide a corresponding health question record 133 which identifies, for example, the question, the answer provided, and/or whether the question was answered correctly. The health question record 133 can also specify a topic or topics of the question.

According to some embodiments, the question identified with the health question record 133 can be associated with a health parameter value 151. As described by other examples, the health parameter value 151 can be determined as part of a correlative model that is developed using a control population in order to provide a quantified correlation to physiological or mental health. A health scoring data store 150 can maintain a collection of health parameter values 151 for individual questions. In one implementation, the health parameter values 151 reflect a predefined health outcome. Multiple health outcomes can be considered, and each question of health question record 133 can be associated with a particular health outcome. By way of examples, the possible health outcomes that have quantifiable correlations to the health parameter values 151 include (i) health care cost for an individual in a given time period, (ii) number of medical facility visits by an individual in a given time period, (iii) number of prescriptions that the person takes in a given time period, and/or (iv) number of sick days that the person took. Other examples of health outcomes include propensity for cancer (including cancer of different types), heart disease, diabetes, hypertension or other afflictions. The health outcomes can thus be numerical and continuous in nature (e.g., health care cost) or categorical (e.g., number of medical visits, prescriptions, sick days).

Accordingly, in one implementation, the health scoring component 140 utilizes health outcome logic 142 to generate a health outcome score 165 that is specific to a particular health outcome definition 155. The health outcome logic 142 can be implemented as a formula or model, and can take into account parameters that include the health parameter value 151 determined an answered question, the number of questions answered, the time of involvement, etc. In one implementation, the health parameter values 151 that can be combined or tabulated can be determined from identifying the health questions 141 and responses 143 of the user. Based on the question and response the health correlative parameters 151 are retrieved.

In an embodiment, the health scoring component 140 uses the health correlation parameter 151, as well as the question 141 and response 143 to predict the health outcome 165 of the user. In determining the health outcome, the health scoring component 140 can use a model or formula to determine the health output score 165. For example, the health scoring component 140 can map the user's input to a health score output which is then predictive for the user. The model used by the scoring component 140 to predict the health outcome score 165 of the user can be the same model which determines the correlation of questions to the particular health outcome definition. Examples of such models is provided with FIG. 2.

The health outcome score 165 can be generated and stored as part of the user health data store 160. Additionally, the health outcome score 165 can be specific to a particular health outcome, and the type of value it reflects can be specific to the health outcome type. For example, one implementation provides that for a health outcome that reflects health care cost for the individual, the health outcome score 165 can be a numeric indication of a specific cost or range of costs for the individual. The health outcome score 165 for the number of medical facility visits, on the other hand, can be reflected by a category or level (e.g., 1 to 5 depending on amount).

In one implementation, the user health data store 160 is maintained logically or physically separate from the question response data store 118 in order to preclude its viewability to users of the system 100. Each user can include a profile of health outcome scores with the user health data store 160, with individual user profiles 141 which include scores for multiple different health outcomes. In some variations, a combined score or category may also be given to individual users as part of their health profile.

As described with other embodiments, the health outcome score(s) 165 of the user can be made available for health services, such as health insurance services. For example, the premium, deductible or scope of coverage provided as part of a health insurance package for a user can be determined from the health outcome score(s) 165. As another feature, health outcome score(s) 165 of the user can be used to determine if the user should receive a discount for health insurance, or alternatively receive an added benefit from health related services that are provided (or are to be provided) to the user.

According to one embodiment, a health service 190 sub-system can utilize the health outcome scores 165 provided in the user health database 160 to determine designations, qualifications or service level, in connection with a health-related service. Examples of health related services 190 include health insurance, life insurance, health service plans, memberships in health related facilities (e.g., health spas, medical office), informational services (e.g., magazine or journal subscriptions, electronic news). The benefit that can be provided to the user includes the service itself, or alternatively a designation of health for use with such a service. For example, the user's predicted level of health can be determined by the health outcome score(s) 165, and this can result in an overall health outcome determination (e.g., a ranking or classification), which in turn can be used to receive a discount for health related services (e.g., discount on health or life insurance premium, expanded coverage, etc.). An example of health service sub-system is provided with an example of FIG. 6B.

In some implementations, the user interface 110 of system 100 can include various layers or functional components for enhancing the interactivity level of the user. In one implementation, the user interface 110 includes a gamification layer 112 and a community social network layer 114. The gamification layer 112 includes logic, data, and content (collectively "game data 103") for implementing a competitive environment for which the individual is to supply answers for questions 127. The game data 103 can be generated a gaming engine 115, which can further personalize the gaming environment for the specific user. For example, the user identifier 121 can be used by a gaming engine 115 to generate user-specific game data 103. The game data 103 can, for example, include a competitive environment that is based on the knowledge level of the user and/or topical interests of the user. An implementation that utilizes a gamification layer 112 is described with FIG. 7A. The gamification layer 112 can determine awards or credentials (e.g., skill level badges) for the user based on their performance. By way of example, the questions 127 presented through the user interface 110 can be associated with a score value that accounts for difficulty (which may be determined from a calibration process, as detailed below), response time, handicaps (e.g., the age of the user), etc.

The community social network layer 114 can operate using community data 117, which can be generated from a community/social network service 116. The community/social network service 116 can, for example, provide user-specific community (or social network) data based on the user identifier 121. The community data 117 can provide content (e.g., user's health interest or knowledge specialties) that is provided as part of the community social network layer 114.

The health parameter value 151 represents a correlative and quantified measure as between human health and knowledge of a particular assertion. The granularity of the health parameter value 151 is applied to a question as answered from an individual, but the determination of the value can be based on a correlative model applied to a control population of users. The control population of users include those individuals who, for example, voluntarily provide real-world information about themselves, and more specifically, actual health outcomes in a recent duration of time.

In more detail, system 100 can include a question analysis sub-system 170 that includes functionality for determining correlations between knowledge of individual questions and actual health outcomes. The sub-system 170 can implement and develop one or more correlative models 172, which can analyze input questions 171 for purpose of determining correlations to health outcomes. In particular, the correlative models can be implemented for purpose of determining health parameter values 149 that statistically reflect a correlation as between knowledge of individuals in the control population (shown with the control population data store 180) for particular question and the respective health outcomes for those individuals who answered the question (either correctly or incorrectly, depending on implementation). The health correlative values 151 can be specific to individual questions or cluster of questions. In one implementation, different correlative models 172 can be used for different types of health outcomes. Different correlative models may compare a predicted value with actual (or real-world) data provided for individuals (shown as verified input 175). An example of question analysis sub-system is described in more detail with an example of FIG. 2.

While numerous examples provide for use of health correlative scores, other embodiments can also generate recommendations to users based on their overall knowledge level, as determined by, for example, the user's score, or topic-specific scores. A response analysis 164 can retrieve scores 145 from the response database 118, for example, and generate recommendations, content or other output based on the user scores. An example of response analysis 164 is illustrated with FIG. 7B, and accompanying examples thereof.

As an addition or alternative, the community social network layer 114 can provide forums such as message boards, ask an expert, or topical walls for shared information and experiences. In one implementation, credentials that the user earns through the gamification layer 112 are carried onto the social environment of the community social network layer 114. For example, an 'expert level' user may have credence when responding to questions of others, even to a point where the user can request payment or other consideration for providing answers or information to other users.

Figures 2, 3:
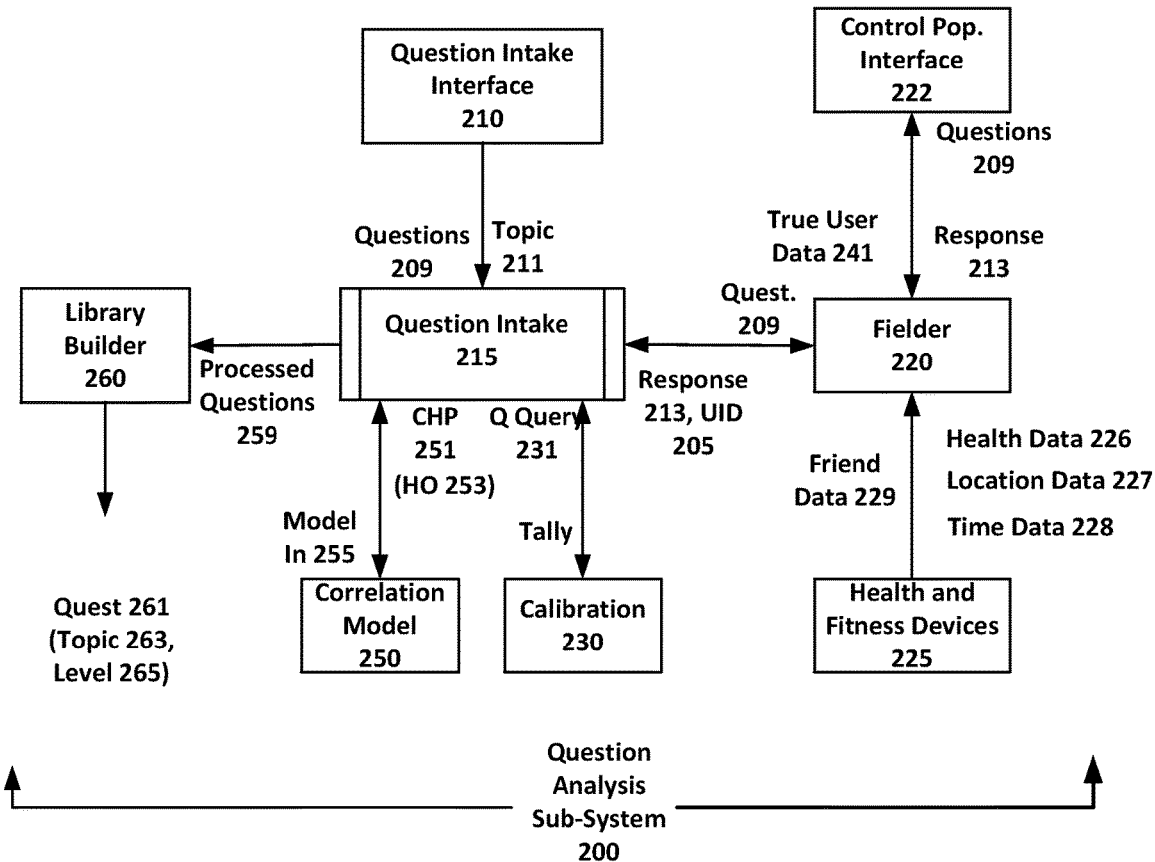
FIG. 2 illustrates an analysis system, according to an embodiment.
FIG. 3 illustrates an example of a data structure that can be developed to link a question with a health outcome and a topic, according to one or more embodiments.

FIG. 2 illustrates an analysis system, according to an embodiment. In particular, FIG. 2 illustrates an analysis system 200 for analyzing questions (or other forms of assertions) for purpose of determining whether knowledge of the underlying assertions by subjects can be correlated to physiological or mental health of the subjects. According to some embodiments, individual questions, or alternatively groups of questions, can be correlated to a quantifiable metric that statistically relates a subject's knowledge (or lack of knowledge) for an underlying assertion to a likelihood of a particular health outcome. The system 200 can be implemented as, for example, a sub-system of a physiological/mental predictive system 100, such as shown with an example of FIG. 1.

In more detail, system 200 includes a question intake interface 210, a fielder 220, a calibration component 230, and a correlative model implementation component 250. A question interface can receive questions 209 through, for example, a manual interface (e.g., experts generate questions based on health assertions). The questions 209 can be manually associated with one or more topics relating to human health, such as topics relating to nutrition or exercise, or specific medical conditions. The granularity of the topics 211 can be determined by implementation. A question store 215 can be used to store a question 209 for processing as the question is calibrated and/or correlated to human health.

The fielder 220 includes functionality to distribute the questions 209 to a control population of users through a population interface 222. For example, the fielder 220 can issue questions using the user interface 110 of an example system of FIG. 1. For example, with further reference to an example of FIG. 1, questions 209 can be issued through gameplay of user interface 110, and responses from various users can be recorded. Some users, however, can be designated as belonging to the control group. These users can correspond to individuals for which data corresponding to ground truth data exists. For example, many users can be given an opportunity to volunteer real-world health information. Such users can be asked questions such as "how many doctor visits did you have last year" or "how many sick days did you have last year." Still further, some information like the user's health insurance cost can be obtained from a source such as the insurance companies. Accordingly, in one example such as shown by FIG. 1, members of the control group can supply responses 213 to questions 209, presented through a game. At a separate time, either before or after the questions 209 is presented to the subject, the subject can also be given the choice to provide actual data, shown as true user data 241. The true user data 241 can represent an actual health outcome of a subject providing the response 213. The true user data 241 can include information manually supplied by the subject, as well as information provided by, for example, an insurance carrier of the subject. Each response 213 from one of the subjects of the control population (e.g., those users of system 100 who opt-in to provide information) can be linked to the question and to the identifier 205 of the subject. Additionally, the true user data 241 can be linked to the user identifier 205 of the subject providing the response.

In addition, true user data 241 can be supplemented or replaced with information gathered by activity monitoring devices 225 in order to create more accurate control data. Activity monitoring devices 225 can provide health data 226 from sensors, such as heart rate and heart rate trends, calories burned, active minutes, sleep quality, blood sugar, or cholesterol levels. Location data 227 can also be provided and includes where a user is located based on GPS data, which can be used in conjunction with other databases to determine, for example, if a user is in a restaurant, grocery store, etc. Furthermore, time data 228 can be used to track a user's schedule. In addition, a user can also choose questions to send to a friend through their activity monitoring devices 225 as friend data 229.

In some embodiments, some or all of these data gathered from activity monitoring devices 225 can be used by fielder 220 to choose which questions 209 are presented to a user. For example, if health data 226 shows that a user has high blood pressure, questions relating to how to lower blood pressure can be chosen. If the user is shown to have poor sleep quality, questions about tips to get better sleep can be chosen. If the user has just finished a workout, questions about post-workout recovery can be chosen. If a user is determined to be a new runner, questions about basic running knowledge can be chosen, whereas if a user is an advanced runner, more advanced questions can be chosen instead.

Location data 227 and time data 228 can also be used by fielder 220 to interpret a user's schedule and choose appropriate schedule-related questions. For example, if the data show that a user commutes via a long subway ride every weekday, questions about exercise ideas for long commuters can be shown. If a user is detected in a restaurant, questions regarding healthy food choices can be shown, and if a user is in a grocery store, questions about vegetables, organic food, and nutrition can be shown.

The calibration component 230 can analyze the questions 209 under process to determine a difficulty level 265 of the question. For example, the calibration component 230 can query 231 the intake store 215 for a tally of the number of responses which were correct and incorrect. The percentage of individuals who correctly answer a question can provide a basis for determining a difficulty level of the question. The difficulty level 265 can be stored with the question for subsequent use.

The correlation model 250 operates to determine a correlation between knowledge by a subject for an underlying assertion of a question and the subject's health. In one implementation, the correlation model 250 implements one or multiple models for purpose of determining different parametric values that statistically correlate to different health outcome definitions (e.g., amount of healthcare or healthcare cost an individual requires, the number of medical facility visits, propensity for heart disease, cancer, hypertension or diabetes, etc.). The correlation model 250 can receive, as model input 255, (i) a question identifier 261, (ii) identification of a set of individuals in the control group who answered the question 209, including identification of the answer each person provided to the question 209, and (iii) true user data 241 for each person in the set of individuals that answered the question. The particular model selected compares an expected result to a true result by (i) assigning the person to an expected result, corresponding to a particular health parameter value, based on their answer to a question, then (ii) using the true user data 241 to compare a true health outcome (reflecting real-world data of the individual supplying the answer) to the expected result.

The expected result can initially start as a hypothetical or neutral value, indicating a likelihood that a given person has or does not have a particular health outcome based on the answer the person provided to the question. The expected result can further include different values depending on whether the user provided a correct answer or incorrect answer, as well as which incorrect answer the user provided. The initial correlation can correspond to a coefficient (e.g., a value between 0 and 1) that is set by, for example, an expectation as to whether the underlying assertion of the question is information that is indicative of health-conscious behavior (e.g., rubbing one's eyes can make a person susceptible to common cold) or information that is indicative of poor health-conscious behavior (e.g., specific nutritional information about a donut). From the initial value, the correlation can become positive, negative or made neutral based on the expected/actual comparison for persons in the set. As more individuals are added to the set, the correlation can be made more valid or certain. The determined correlation from the correlation model 250 can be identified as correlative health parameter 251. The correlative health parameter 251 can be specific to a particular health outcome 253. The correlative health parameter 251 can, for example, correspond to a parametric value, such as a weight or coefficient, which can be aggregated, modeled and/or combined with other parametric values to make a health outcome determination.

The particular model 255 implemented by correlation model 250 can depend on the nature of the health outcome that the assertion is to apply to. For a health outcome definition in which the health parameter value is continuous (e.g., monetary cost for health care in a given period, weight or body mass index), a linear regression model can be used. Some health outcome definitions can utilize health parameter values which are tiered or categorical. For example, the number of medical facility visits can be defined into tiered values, such as: 0=no medical facility visits, 1=1-2 medical facility visits in a year, 2=3-5 medical facility visits in a year, or 4=5 or more medical facility visits in a year. Similar tiered values can be used for health outcomes such as sick days. For such health outcomes, an ordinal logistic regression model can be used. In variations, a multinomial or polynomial model can be used for tiered categories, particularly those health outcomes which define tiers which are not naturally ordered. Each question can be assigned to a particular health outcome, so that the health parameter value is specific to the determination of the health outcome.

Numerous other machine-learning models can be used in both developing correlative health parameters, and determining health outcomes based on correlative health parameters. By way of example, such machine-learning models can include random forest, neural network and/or gradient boosting models.

In some embodiments, the determination of the health parameter values 251 can be tuned to reflect determinations that are for use with a model in which no user-specific information is known. In one implementation, the control population can be associated with classification parameters, such as age group (e.g., over 50, under 50), gender, weight, race, geographic location or setting, and/or presence of certain medical conditions such as diabetes. An individual question can be associated with multiple correlative health parameter values 251, including health parameter values that reflect the general control population, as well as a health parameter value that is specific to a class or sub-class (e.g., females over 50).

According to some embodiments, a combination of question and correlative health values 251 can map to one of multiple possible health outcomes. Thus, in one implementation, a question can have a correlative health value as it applies to a single health outcome.

Other implementations provide for the determination of health parameter values 251 which are correlative to health of a user based on a model in which a classification (e.g., gender or age) or set of classifications (e.g., gender and age) are known about the person answering the question. Depending on implementation, the classifications of users can include (i) unknown users, for which no information is known, (ii) users for which some basic health-relevant characteristic is known, such as age, gender, or combination thereof, (iii) users for which multiple relevant facets of health is known, such as their weight and/or height, as well as, as gender and age. One implementation provides for the determination of correlative health parameters 251 which are determined specific for different classifications of the user, based on applying models as described to segments of the control population which have the relevant classification. Thus, in some variations, the correlative health parameter values 251 can be made specific to specific classes of persons, so that the evaluation of health for the user is made in reference to the user's class. For example, in some embodiments, the questions can be fielded for individuals who categorize themselves by gender, age, weight, and/or presence of certain medical conditions such as diabetes.

System 200 can be implemented on a control group that is dynamic, meaning individuals can be added to the control group continuously over time. As mentioned, a larger control group can provide more valid results. In an interactive gaming environment, such as described with an example of FIG. 1, additional persons can be added to the control group continuously through invitation or opt-in features. For example, the user-interface 110 can prompt individuals to volunteer for questions that reflect actual medically relevant information. This mechanism can provide a way to expand the control group with the addition of users for whom true user data 241 can be provided. The control group can also be managed based on criteria, such as gender and age, so that it accurately reflects a desired population segment.

With the determination of the health parameter values 251, the questions can be deemed processed, in which case the questions can be included in a library or collection of questions and marked as being correlative to health. In one implementation, a library build process 260 links processed questions 259 with the question identifier 261, topical identifier, the difficulty level 265 and the correlative health parameter 251 (or multiple values). The difficulty level 265 can be used to determine which individuals receive the question based on user level.

While an example of FIG. 2 provides for processing of questions which are deemed correlative to health, a fielding and calibration process can be used to determine difficulty of all questions, including those questions which have no determined correlation to health. For example, any question can be associated with the topic 211 and fielded to the control population as described, and further evaluated for difficulty level 265 based on, for example, the percentage of individuals of the control group who correctly answered the question.

FIG. 3 illustrates an example of a data structure that can be developed to link a question with a health outcome and a topic, according to one or more embodiments. While an example of FIG. 3 illustrates the data structure 300 as being logically integrated, variations can provide for distributed data structures which associate or link parameters as described. With reference to an example of FIG. 1, the data structure 300 of an example of FIG. 3 can, for example, be provided with the question library 152, and include information provided with the health scoring database 150.

In more detail, data structure 300 associates individual questions by question identifier 301 to one of multiple possible correlative health parameters 303, and one or more topics 305. Other information or parameters that can be conveyed with the data structure 300 include a difficulty level, which can be determined, for example, through an output of the calibration component 230 (see FIG. 2). For a given implementation, the correlative health parameter can relate to a particular health outcome. Multiple health outcomes can be defined for a future time interval, including health care cost, medical facility visits, sick days, and number of prescriptions. Other examples of health outcomes include blood sugar level, weight or body fat (e.g., BMI), cholesterol level, depression or anxiety disorder, and/or longevity. In one embodiment, each question associated to only one health outcome, and is further assigned a correlative health parameter value that reflects a correlative measure between knowledge of the underlying assertion and a corresponding health outcome. In one implementation, a system of FIG. 2 determines health parameter values for each defined health outcome, and the health parameter value selected for a question is that which has the strongest correlation. If no correlative health determination has been made for a question, then the health parameter values for such questions can be shown as null.

As further shown by an example of FIG. 3, each question can be linked with multiple topics based on, for example, manual input. The determined difficulty can also be expressed as a parameter, such as a number between 0 and 1. The difficulty level can be independent of the topic assignment for the question-thus, meaning the difficulty level of a question can be provided as being the same regardless of the assigned topic being considered.

Methodology

Figure 4:
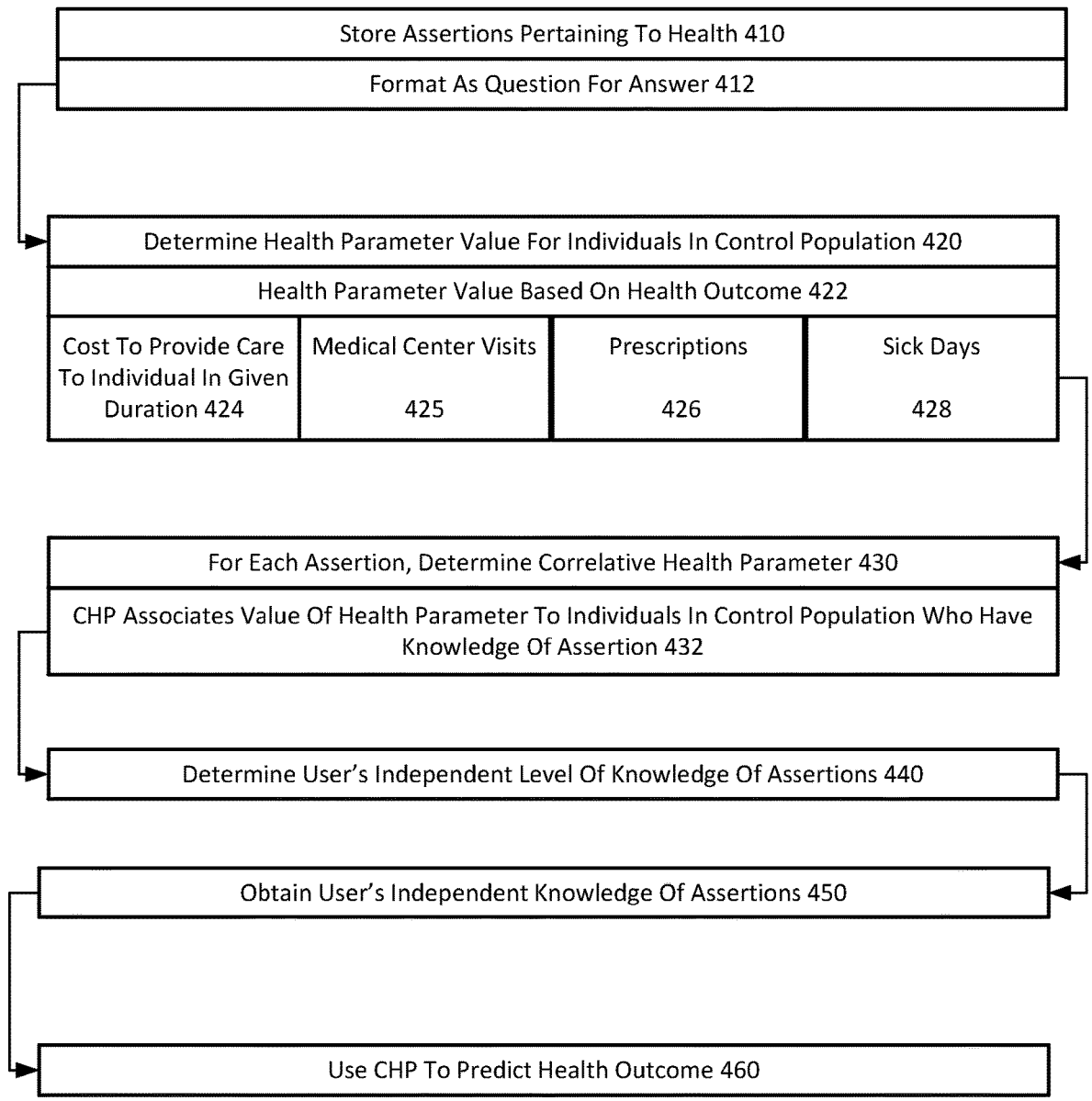
FIG. 4 illustrates an example method for predicting a health outcome of a user based in part on whether a user has independent knowledge of an assertion relating to health.
Figure 5:
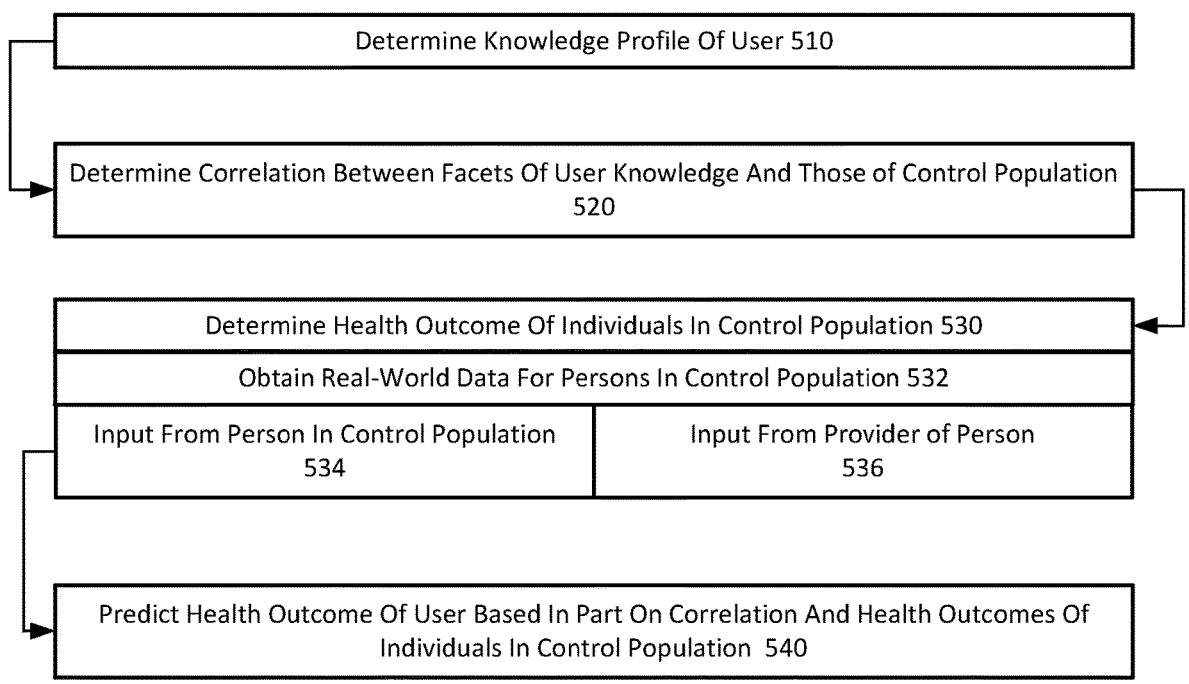
FIG. 5 illustrates an example method for predicting a health outcome of a user based on a knowledge profile of a user.

FIG. 4 illustrates an example method for predicting a health outcome of a user based in part on whether a user has independent knowledge of an assertion relating to health. FIG. 5 illustrates an example method for predicting a health outcome of a user based on a knowledge profile of a user. In describing example methods of FIG. 4 and FIG. 5, reference may be made to elements of FIG. 1, FIG. 2 or FIG. 3 for purpose of illustrating a suitable component for performing a step or sub-step being described.

With reference to an example of FIG. 4, a collection of assertions relating to human health can be stored and processed for use with a population of users (410). In one implementation, the assertions can be formatted as questions for which the answer from the user indicates whether the user has knowledge of the assertion (412).

For the control population, a health parameter value is determined for individuals of the control population (420). The health parameter value can reference actual or real-world data which serves as an indicator of physiological or mental health of a user. In one implementation, the determination of the health parameter value can be based on input of a user. For example, in an interactive gaming environment of FIG. 1, some users can opt-in to provide requested health-specific input, such as the number of sick days taken in the prior month or year. In some embodiments, the health parameter value is based on a defined health outcome (422), or combinations of health outcomes. By way of example, the health outcome can correspond to an estimated health care cost for an individual (424), a number of medical center visits for an individual in a given duration of time (425), a number of prescriptions for the individual in the given time frame (426), and a number of sick days an individual incurred in the given duration of time (428).

For each assertion, a correlative health parameter is determined (430). Generally, the correlative health parameter corresponds to a parametric measure that quantifiably links knowledge of an assertion to human health. The health parameter value 151 (FIG. 1), 251 (FIG. 2), as described with other examples, provides an example based on use of a control group (432).

The establishment of questions with associated correlative health parameters can be done through implementation of a model, with ground truth data provided by select users from a larger user base of respondents. Once the correlative health parameters are established for individual questions, the questions can be fielded to the user base. The responses from the user can be used to determine the user's independent knowledge level of a particular assertion (440).

The correlative health parameters for the individual questions answered by the user can be determined and modeled into a value for a particular health outcome (450). For each user, the correlative health parameters of the answered questions pertaining to a particular health outcome can serve as inputs in order to determine a predicted health outcome for the user (460). Multiple health outcomes can be determined in this manner.

With reference to FIG. 5, a knowledge profile of a user can be determined, relating to a particular health outcome (510). The knowledge profile can reflect answers to individual questions, or answers to clusters or groups of questions. The knowledge profile can be determined based on a selected definition. In one implementation, the knowledge profile is specific to a question, and reflects whether a user correctly answer the question. In a variation, the knowledge profile is specific to a question, and reflects which question the user answered. Still further, the knowledge profile can reflect the user's answers in aggregate form, such as in a cluster of questions (e.g., 3 to 10 questions), reflecting facets such as the number of questions the user correctly answered in the cluster, or the number of answers provided which were deemed more wrong than others.

A facet of the knowledge profile can be compared to corresponding facets of knowledge profiles from individuals of a control group (520). In one implementation, the user's answer to a particular set of questions can be individually compared to an answer to the same set of questions from one or multiple persons of the control group. In variations, the user's answer to a cluster of questions can be compared to answers provided by a subset of the control group for the same cluster of questions, with the comparison being made for the cluster of questions as a whole. Still further, the user's answers can be compared to answers provided by a subset of the control group which provided the same exact answers for the cluster of questions.

A health outcome can be determined for individuals of the control group (530). As mentioned with other examples, the health outcome can be defined as a healthy living style characteristic that is indicative of human health. The health outcome that is determined for a person of the control group can reflect real-world information about that person (532). In one implementation, individuals of the control group can volunteer their personal health outcome information (534). For example, the information can be provided in exchange for some benefit to the person of the control group. In other examples, personal health outcome information for persons in the control group can be determined using data from activity monitoring devices. In variations, the health outcomes information for persons of the control group can be determined from sources such as health care or insurance providers (536).

The health outcome of a user can be predicted based in part on a correlation between the health outcomes of individuals in the control population and the compared facets of the knowledge profile between the user and persons of the control group (540). Thus, for example, a user's answer to individual questions can be compared to the answers provided for the same questions by those members of the control group. As an addition or alternative, a user's answers to a cluster of questions can be compared to answers provided to the same cluster of questions for individuals of the control group, with, for example, the comparison being based on matching the user with a subset of persons of the control group based on a percentage of correct or incorrect answers provided.

Health Service Methodology and Sub-System

Figure 6A:
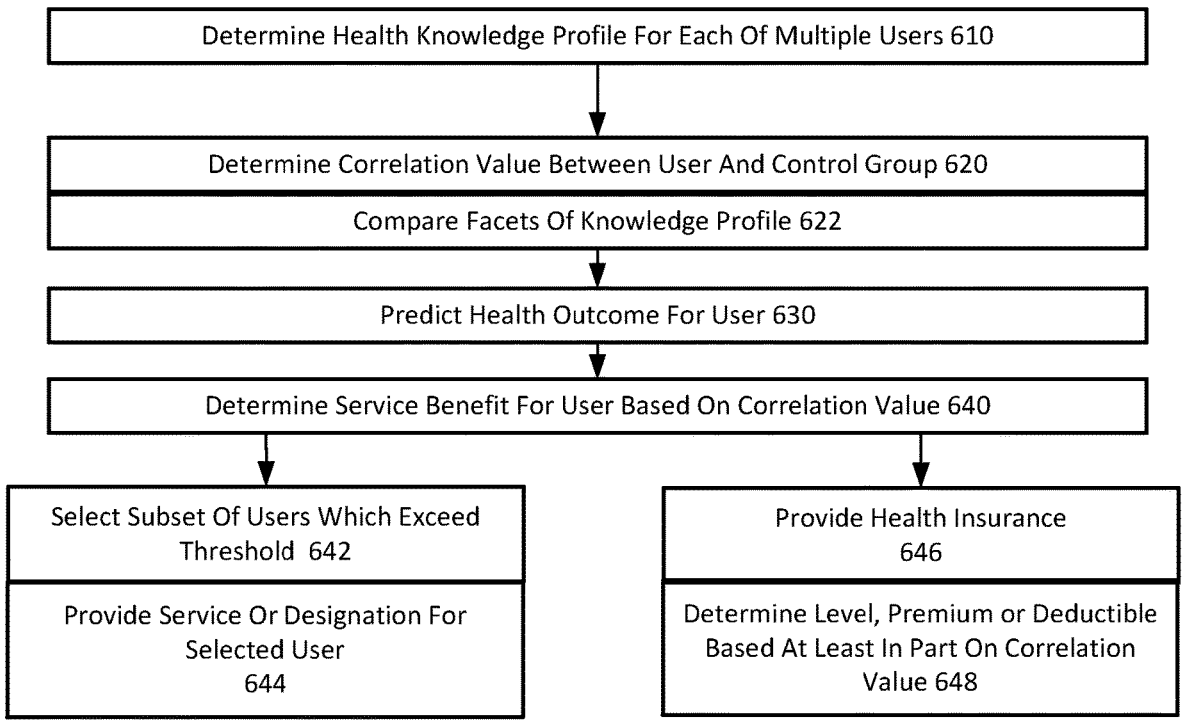
FIG. 6A illustrates an example method for providing a health related service to a user based on a knowledge-predicted health outcome for a user.

FIG. 6A illustrates an example method for providing a health-related service to a user based on a knowledge-predicted health outcome for a user. In describing example method of FIG. 6A, reference may be made to elements of FIG. 1, FIG. 2 or FIG. 3 for purpose of illustrating a suitable component for performing a step or sub-step being described.

With reference to FIG. 6A, a health knowledge profile is determined from each of multiple users (610) with regard to assertions relating to health (e.g., physiological or mental health). As mentioned with other examples, the health knowledge profile can reflect individual answers to questions, those questions which were answered correctly or incorrectly, specific answers provided to specific questions (e.g., such as incorrect answers), and/or percentages of questions answered from a defined cluster of questions.

Additionally, as mentioned with other examples, a value of a health correlation parameter can be determined as between the user and a subset of persons in the control group (620). With reference to an example of FIG. 1, the health value parameter 151 can, for example, be determined by the health scoring component 140. In determining the health correlation parameter, a given facet of the users' knowledge profile can be compared to that of relevant persons in the control group (622). By way of example, the comparison can be on a question by question basis, or alternatively, on a cluster basis (e.g., compare set of 5 answers, etc.). Actual health outcomes can be known for members of the control group, and the identified correlative health parameters can be based in part on the known health parameters of individuals in the control group. The correlative health parameter can thus be pre-determined for the control group, and based on real-world information about members of the control group.

Based on the correlation values, a health outcome determination is provided for the user (630). As shown with an example of FIG. 3, the correlation values can be specific to pre-determined health outcomes. Further with reference to an example of FIG. 1, given a set of health parameter values 151 for a particular health outcome, the health scoring component 140 can make a health outcome determination. The determination of the health outcome can be in the form of a score, so that it gives a relative measure of the particular health outcome as compared to other individuals in the general population. The health outcome determination can correspond to a health outcome score 165, or alternatively, to a combination of health outcome scores. For example, multiple health outcome scores can be determined for the user, and the scores can be combined to form an aggregate health outcome determination.

Based on the health outcome determination, a health service benefit can be provided to the user (640). The service or designation can be one made for a set value, wherein the service or designation is associated with a true per-user cost that is not equal to the set value, but which is variable and set to increases over time when individual users in the subset suffer negative health consequences as a result of a naturally progressing medical condition.

The health service benefit can correspond to a variety of direct and indirect service related benefits. In one implementation, those users with a health outcome determination that exceeds a particular threshold can receive a designation (642). The designation can correspond to a service or credential provided to only select users of, for example, a network service provided with system 100 (644). For example, those users which receive a health outcome determination that places them within the top 10 percentile of all users may receive a certification, which in turn enables them to receiving discounts with their healthcare provider, health insurance, or related health service activities (e.g., discount with nutrition store, athletic gym membership, life insurance, etc.). Alternatively, the designation can entitle the subset of users to receive a service, such as primary health insurance, supplemental accidental insurance, life insurance, or other membership service (whether health related or not).

In variations, the health outcome determination provides a basis for predicting a user's health, and this basis can in turn be used to determine health related services for the user (646). For example, health insurance, life insurance, and/or accidental health insurance can be provided to the user with scope and cost determined by the health outcome determination. For example, the cost of the premium or deductible to the individual user can be based on the health outcome determination (648). By way of example, an insurance service can be provided to users of system 100, and those users with better health outcome determinations can be provided discounts to their premiums or deductibles, or alternatively given greater scope of coverage as compared to counterparts users who have lesser health outcome determinations.

Figure 6B:
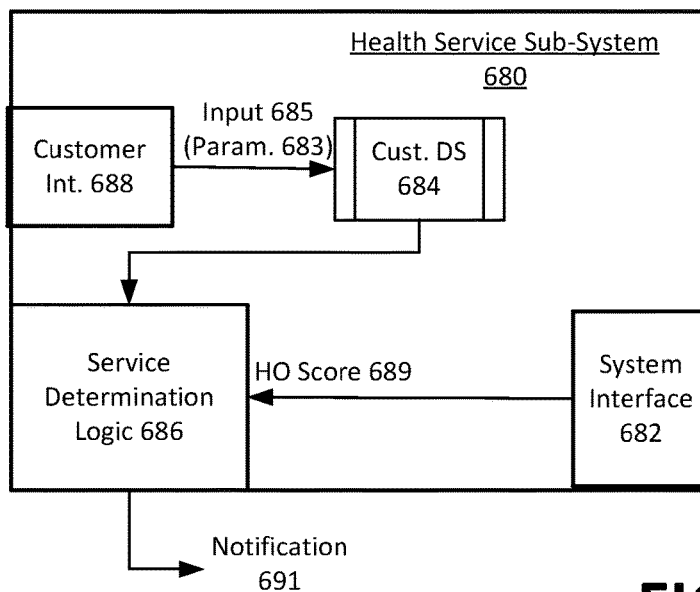
FIG. 6B illustrates a health service sub-system 680, according to an embodiment.

FIG. 6B illustrates a health service sub-system 680, according to an embodiment. A health service sub-system 680 can be implemented with or as part of, for example, system 100. In variations, the health service sub-system 680 can be provided as a separate system which interfaces with the system 100. Additionally, the health service sub-system 680 provides an example of a system on which an example of FIG. 6 can be implemented.

With reference to FIG. 6B, a health service sub-system 680 includes a system interface 682, a customer data store 684, and service determination logic 686. The health service sub-system 680 can also include a service customer interface 688, such as a web page or application page, which a service customer accesses to provide input for defining the health service offered, as well specific logic or parameters for the service determination logic 686. The service customer input

685 can, for example, include text data definition of the service offered (e.g., terms of health or life insurance), as well a supplemental content for viewing by users of system 100. This input can be stored in the service data store 684.

In some variations, the service customer input 685 can further input parameters 683 and other logic (e.g., rules) for the service determination logic 686. The parameters 683 and rules can, for example, including definition of the qualifications needed for users to (i) receive the service, (ii) receive a particular facet or tier of the service, and/or (iii) receive the service or tier according to a particular price structure. For example, the service can include tiers of benefits, or multi-tiered cost structure, and each tier can be provided to users based on qualifications, such as one or more of (i) a threshold health outcome score or set of scores, (ii) a threshold combination of health outcome score, and/or (iii) other health outcome determination.

The system interface 682 can interface with the user health database 680 in order to determine the health outcome scores 689 of a given user or user-base. In a variation, the system interface 682 can communicate with a push or trigger component on the system 100 which in turn retrieves and pushes specified health outcome scores to the system interface 682. In some embodiments, end-users are precluded from handling health outcome data. The output of health determination logic 686 can correspond to a notification 691, which can specify the results of the health determination logic 686. These results can be communicated to either the user or to a provider of the health service benefit.

Game Play

Numerous embodiments described use of game play and logic as a mechanism to increase use response and participation. More user response and participation can have numerous benefits, including (i) increasing the size of the control group, by finding more qualified volunteers who are willing to provide real-world health information for purpose of developing health correlations to questions, (ii) more predictive correlations based on larger statistical sample, and (iii) data points from users, enabling better prediction of individual user health. Additionally, the use of game logic provides a mechanism to hide health correlative questions from public inspection, thereby precluding users from "gaming" the questions (e.g., studying) for purpose of receiving a good health score.

Figure 7A:
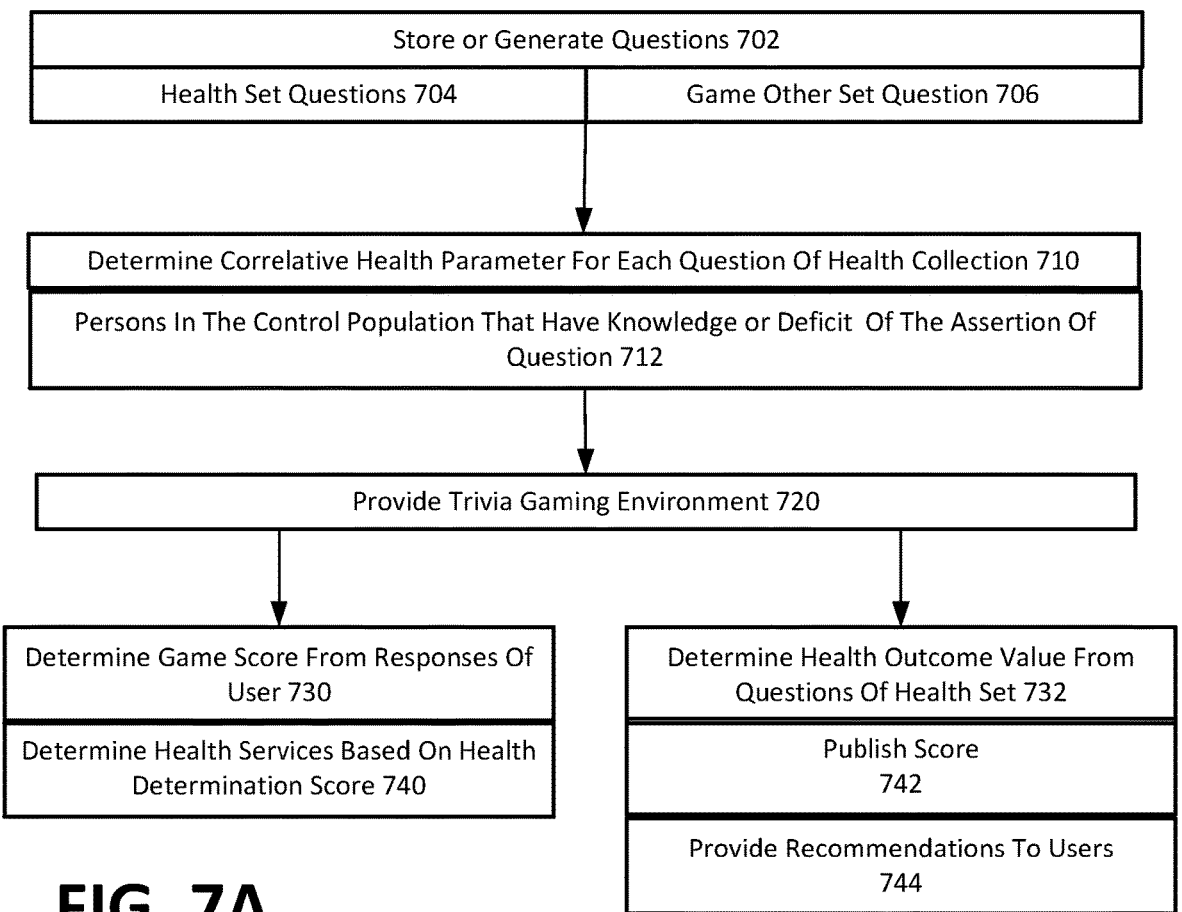
FIG. 7A illustrates an example method for providing a game-based environment in which user responses enable prediction of health outcomes for individual users.

FIG. 7A illustrates an example method for providing a game-based environment in which user responses enable prediction of health outcomes for individual users. In describing an example method of FIG. 7A, reference may be made to elements of FIG. 1, FIG. 2 or FIG. 3 for purpose of illustrating a suitable component for performing a step or sub-step being described.

With reference to an example of FIG. 7A, a set of questions can be stored, were at least some of the questions are based on assertions that are core relative to health (702). For example, questions can be stored in the question library 152, after being processed using a system such as described with an example of FIG. 2. The stored questions can include both (i) health correlative questions, which are used in determining a health outcome score or determination for the user (704); and (ii) non-health correlative questions. While the latter questions may pertain to health, those questions have either not been determined to be correlative or health, or those questions have little relevance to awareness of health, and thus correlative to actual human health (706). As mentioned with other examples, a gaming environment can be implemented in which the questions are provided as trivia, so that users receive entertainment benefit from participating in answering questions.

Still further, as described with other examples, the health correlative questions can be processed to determine a health correlative parameter (710). For example, question analysis subsystem 200 can be used to determine a health correlative parameter 151 for a given question. Still further, as described with other examples, the health correlative parameter can be based on persons in the control population who have knowledge (or knowledge deficit thereof) of an assertion underlying the particular question (712).

In order to encourage participation and development of accurate health outcome scores and determinations, a gaming environment can be established in which users are asked questions in a competitive or semi-competitive context (720). An example of a gaming environment is shown with environments depicted through interfaces of FIG. 8A through 8H.

The user responses to trivia questions are recorded, with those responses including both scores related to health correlative questions (730) and scores related to all questions (or alternatively to non-health correlative scores) (732). As described with an example of FIG. 6, the health correlative questions can be scored for purpose of determining health services to the user (740). This score may be hidden or unknown to the user, and determine independently of the overall gaming score.

Conversely, the overall gaming score can be published in a social or gaming environment, to provide the user with credentials in the community of the service provided through system 100 (742). For example, the user can use the latter gaming score to achieve credentials that give the user authority on message board discussions, and question and answer forums of the community platform.

In some variations, the gaming score can also provide a mechanism to provide health base recommendations to the user (744). For example, the user's knowledge base can be evaluated based on topical subjects, and the user's deficiency or strengths respect to specific topics of health can be used to infer physiological or mental information about the user.

Figure 7B:
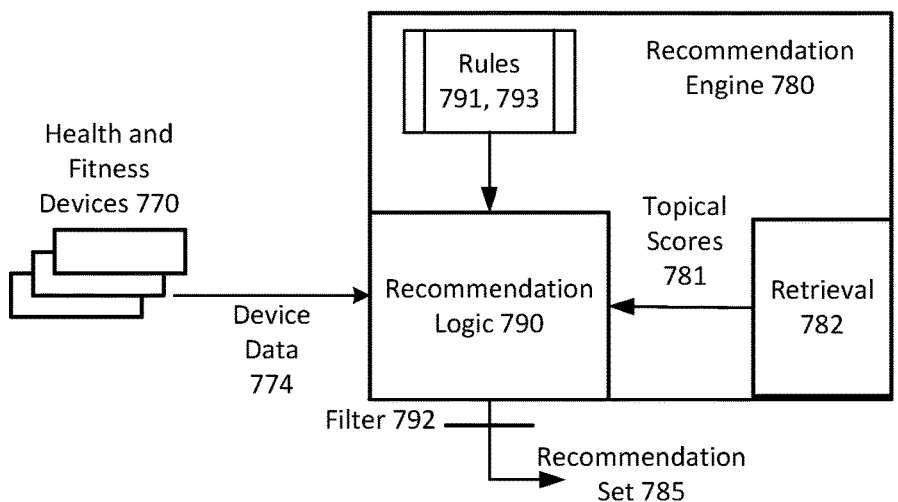
FIG. 7B illustrates a knowledge-based recommendation engine, according to one or more embodiments.

FIG. 7B illustrates a knowledge-based recommendation engine, according to one or more embodiments. With reference to FIG. 1 and FIG. 7B, for example, the response analysis component 164 can include recommendation engine 780. The recommendation engine 780 can use information about the user's knowledge in order to generate recommendations 785, which can include content that communicates to the user specific actions, lifestyle choices, or areas of growth (for knowledge or lifestyle), for purpose of growth.

In one implementation, the recommendations 785 can be based on the determinations of the user's strength or weakness with regards to specific topics of health. The recommendation engine 780 can include processes 782 which retrieve the user's topical scores 781, and then correlate the topical scores with recommendation logic 790. The recommendation logic 790 can include rules 791, 793 for selecting recommendations for the user based on different topical scores and criteria. For example, the recommendation logic 790 can include rules for suggesting recommendations to users for specific topics when the user's score for the topic is below a threshold. By way of example, a topic can be defined for cardiac health, and anytime a user's topical score for cardiac health is below a threshold, a set of recommendations 785 for improving the user's cardiac health can be generated and communicated to the user. Likewise, if the user's knowledge is strong in a particular topic, that can also be interpreted as interest, and the recommendation logic 790 can utilize the score to suggest recommendations that are of an advanced level. For example, if the user scores high in the topic of weight-lifting, then the recommendation provided to the user can include specific techniques or recommendations based on questions that have the highest difficulty level (as determined from, for example, a calibration component 230 of FIG. 2).

In some implementations, activity monitoring devices 770 can provide device data 774, which can include indicators of a user's overall health and fitness levels, to the recommendation logic 790. These devices can include GPS receivers to record statistics like pace, distance, elevation, route history and workout summaries. In addition, they can include sensors such as accelerometers, a gyroscope, a compass, an ambient light sensor, heart rate sensor, among other features capable of tracking and recording health and fitness parameters. Examples of device data 774 include heart rate and heart rate trends, steps, distance traveled, floors climbed, calories burned, active minutes, sleep quality, blood sugar, and cholesterol levels, among others. Recommendation logic 790 can then use device 774, alone or in combination with rules 791,793 and topical scores 781, in order to create the recommendation set 785. For example, if topical scores 781 show that a user has poor knowledge of cholesterol but device data 774 indicates that the user's cholesterol levels are satisfactory, recommendation logic 790 may choose not to recommend cholesterol-related questions.

In a variation, the set of recommendations 785 generated for any one topic can be associated linked with questions or sub-topics of questions. A recommendation filter 792 can filter the recommendations 785, so as to weed out those recommendations the user likely knows based on their correctly answered questions.

Still further, the recommendation logic 790 can include combination rules, which select recommendations 785 for the user based on criterion provided by the user's topical score in two or more topics. The combination rules can identify subject matter relevancy between topics, so that the user's knowledge of one topic will benefit another or vice versa. In one implementation, when the user's topical score of one topic exceeds a threshold, and the topical score of another topic is below a threshold, then the recommendation may be provided that assumes user activity or interest in one topic to assist the user's knowledge or lifestyle with regards to the second topic. For example, the user may have scored high in the topic of weight-lifting, but scored low in nutrition or sleep. The recommendation provided to the user may identify the recommended hours for the user to sleep in order to add muscle mass.

By way of another example, if the user is strong on a subject such as weight training, but poor in nutrition, then the recommendation engine can suggest (i) that the user develop his knowledge on nutrition, (ii) identify nutritional information related to training in order to provide recommendations. Recommendations can include, for example, what the user should eat when training, how such nutritional intake can affect performance in training, recommendations for the user to confirm with a nutritionist, and expected results that can be achieved through proper diet and weight training. Such an example illustrates recommendations that can be made based on the user being strong in his or her knowledge base for one topic and weak in another topic. In such scenarios, the relationship between the two topics can be determined in order to generate programmatically actions and subtopics of learning which may be of interest or benefit to the user.

Similar recommendations can be determined and linked to user's topical scores based on different threshold determinations. In one implementation, if the user scores low on two topics related by subject matter, the user's recommendation may be selected on the assumption that the user suffers from health consequences related to a physiological or mental problem related to the topics.

Still further, analysis of the topical determinations can also be used to infer characteristics about the respondents, without any mathematical correlation being made to the control population. For example, an individual who scores poorly in both nutrition and exercise can be inferred to be obese, potentially diabetic, and/or suffer from other health related issues such as depression. Based on such analysis, the recommendation engine can suggest areas of growth for the user's knowledge. The recommendation engine 780 can also provide recommended actions, such as publishing a diet to the user for weight loss, suggesting the user visits a psychiatrist (on a sound assumption that the user is depressed), suggesting the user sees a nutritionist and/or personal trainer (on the side assumption that the user is overweight), or recommend that the user have his blood sugar checked for diabetes and or high cholesterol. Such actions can follow when the user scores poorly on knowledge in topics that have synergy or relation to one another when considered for physiological or mental health.

Figure 7C:
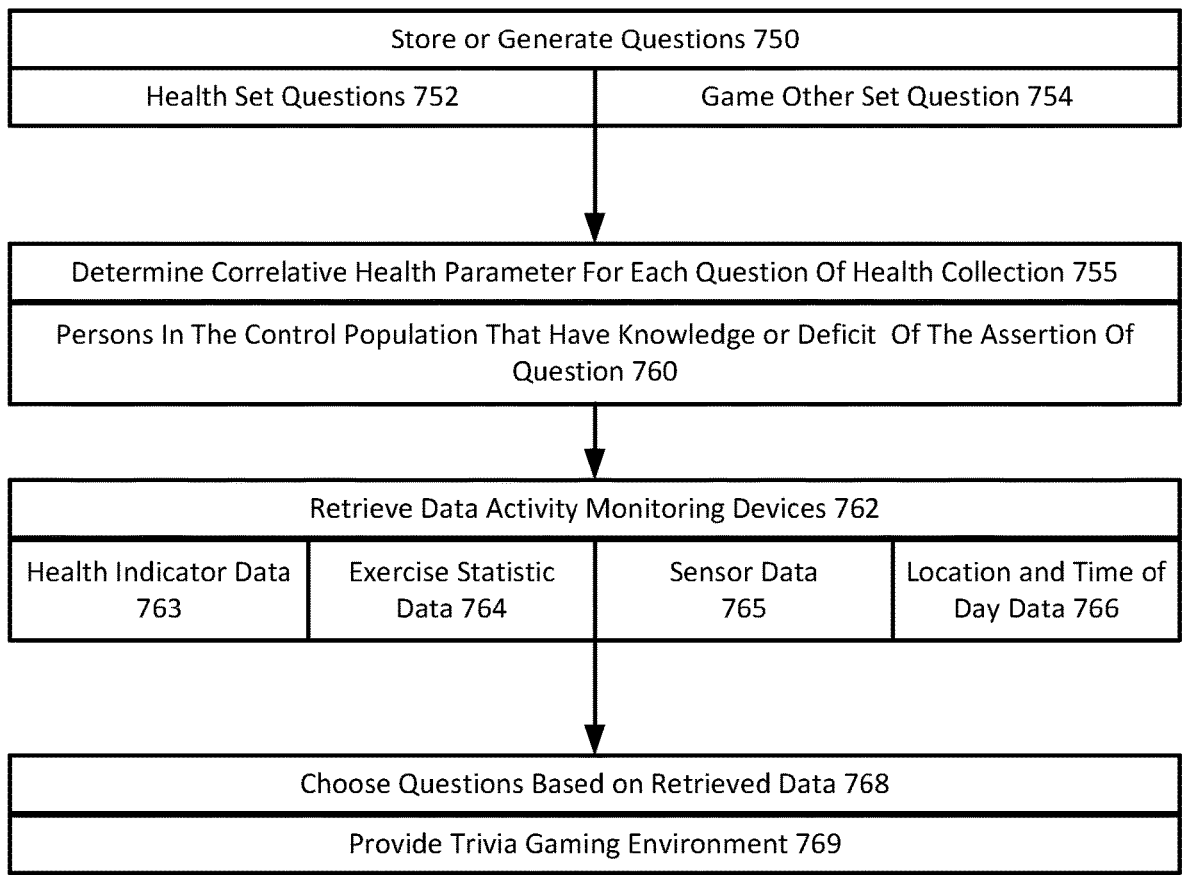
FIG. 7C illustrates an example method for choosing questions to provide to a user based on data retrieved from an activity monitoring device.

FIG. 7C illustrates an example method for choosing questions to provide to a user based on data retrieved from activity monitoring devices. In describing an example method of FIG. 7A, reference may be made to elements of FIG. 1, FIG. 2 or FIG. 3 for purpose of illustrating a suitable component for performing a step or sub-step being described.

With reference to an example of FIG. 7A, a set of questions can be stored, were at least some of the questions are based on assertions that are core relative to health (750). For example, questions can be stored in the question library 152, after being processed using a system such as described with an example of FIG. 2. The stored questions can include both (i) health correlative questions, which are used in determining a health outcome score or determination for the user (752); and (ii) non-health correlative questions. While the latter questions may pertain to health, those questions have either not been determined to be correlative for health, or those questions have little relevance to awareness for health, and thus correlative to actual human health (754). As mentioned with other examples, a gaming environment can be implemented in which the questions are provided as trivia, so that users receive entertainment benefit from participating in answering questions.

Still further, as described with other examples, the health correlative questions can be processed to determine a health correlative parameter (755). For example, question analysis subsystem 200 can be used to determine a health correlative parameter 151 for a given question. Still further, as described with other examples, the health correlative parameter can be based on persons in the control population who have knowledge (or knowledge deficit thereof) of an assertion underlying the particular question (760).

In some aspects, in order to contextually choose questions, question selection 120 can retrieve data generated by activity monitoring devices 191 (762). This can include direct indicators of health such as heart rate, blood sugar, and cholesterol levels (763) as well as information regarding exercise such as steps taken per day, calories burned, and average activity levels (764). These devices typically include sensors such as accelerometers, a gyroscope, compass, GPS, and a light sensor, among others, that can be used to calculate certain health parameters like quality of sleep and distance traveled per day (765). In addition, GPS and clock data can be combined with other health and fitness data in order to determine a user's schedule and where the user is located (766).

After retrieving the activity monitoring device data, question selection 120 can choose questions taking into account the data (768). For example, if health data shows that a user has high blood pressure, questions relating to how to lower blood pressure can be chosen. If the user is shown to have poor sleep quality, questions about tips to get better sleep can be chosen. If the user has just finished a workout, questions about post-workout recovery can be chosen. If a user is determined to be a new runner, questions about basic running knowledge can be chosen, whereas if a user is an advanced runner, more advanced questions can be chosen instead.

Location data and time data can also be used to interpret a user's schedule and choose appropriate schedule-related questions. For example, if the data show that a user commutes via a long subway ride every weekday, questions about exercise ideas for long commuters can be shown. If a user is detected in a restaurant, questions regarding healthy food choices can be shown, and if a user is in a grocery store, questions about vegetables, organic food, and nutrition can be shown.

In order to encourage participation and development of accurate health outcome scores and determinations, a gaming environment can be established in which users are asked questions in a competitive or semi-competitive context (720). An example of a gaming environment is shown with environments depicted through interfaces of FIG. 8A through 8H.

Example Interfaces

FIG. 8A through 8H illustrate example interfaces for use with one or more embodiments described herein. Interfaces such as described with FIGS. 8A through 8H can be implemented using, for example, a system such as described with an example of FIG. 1. Accordingly, reference may be made to elements of FIG. 1 for purpose of illustrating suitable components for implementing an interface as described.

Figure 8B:
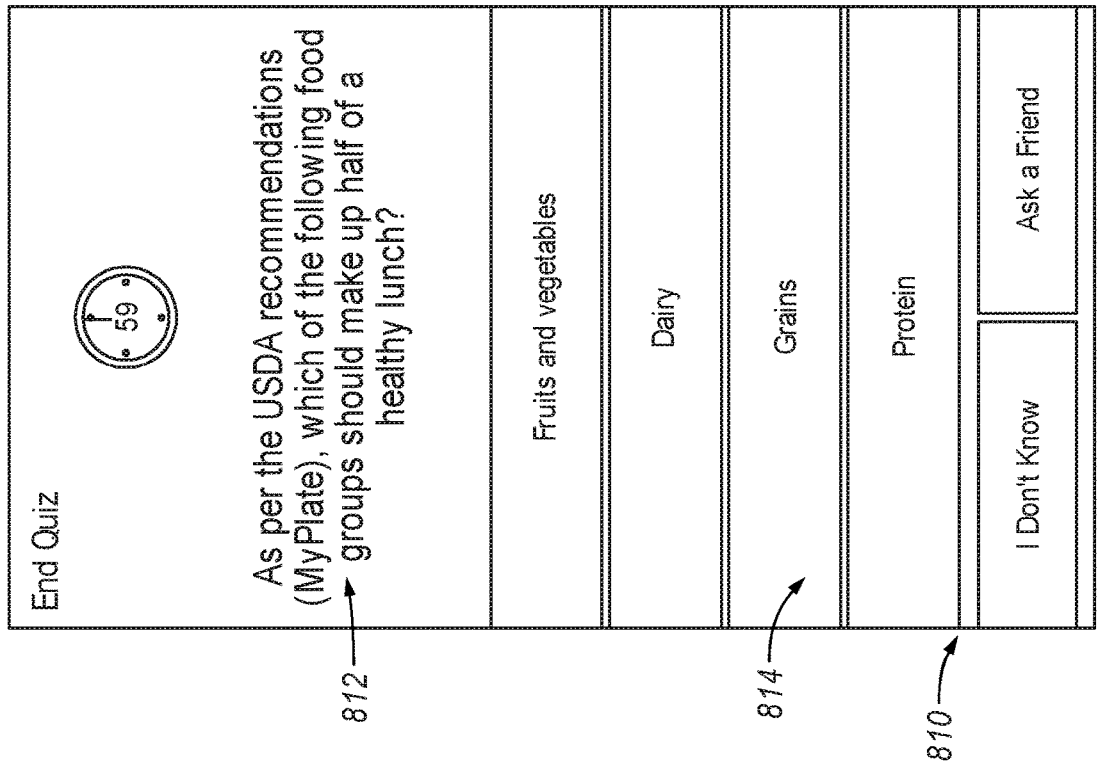
FIG. 8A through 8H illustrate example interfaces for use with one or more embodiments described herein.
Figure 8A:
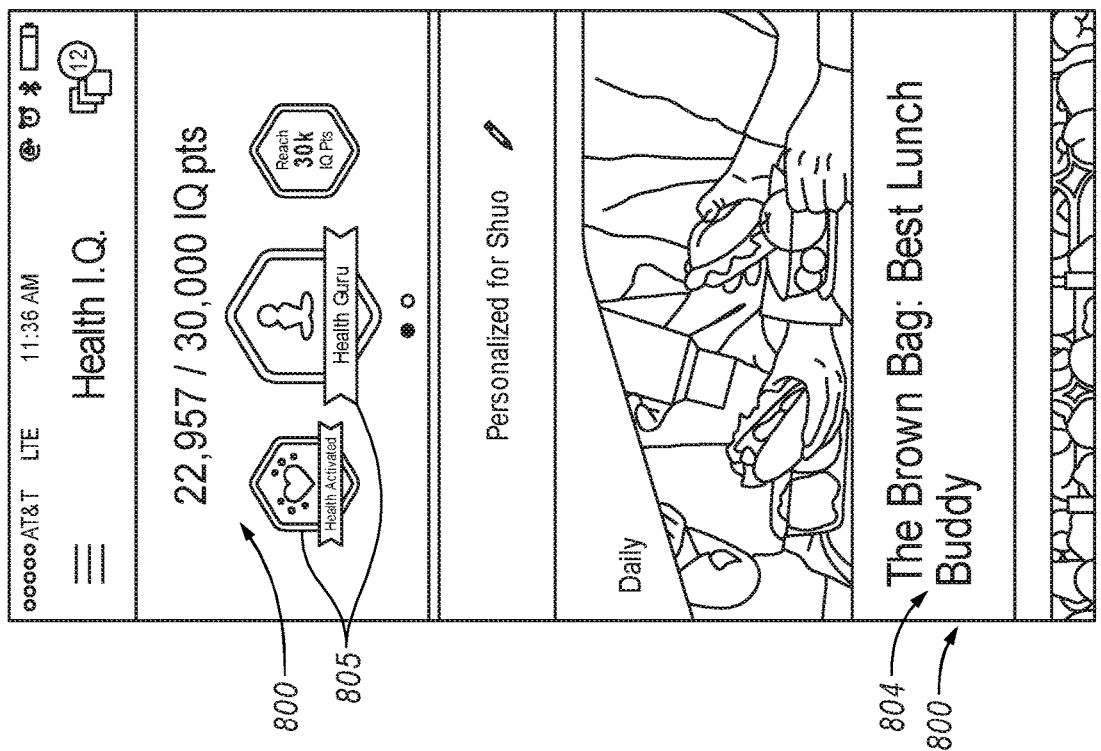

In FIG. 8A, in interface 800 provides a topical selection 804 for a user (e.g., nutrition). The interface 800 can be displayed with information from the user's profile 138, such as their game score 802 (e.g., provided as game data 119 of the user's profile, in an example of FIG. 1) and badges or certifications 805.

The panel 810 of FIG. 8B illustrates a question 812, in the form of trivia. A set of answers 814 can be provided to the user, from which the user can make selection of in order to affect his or her score.

Figure 8D:
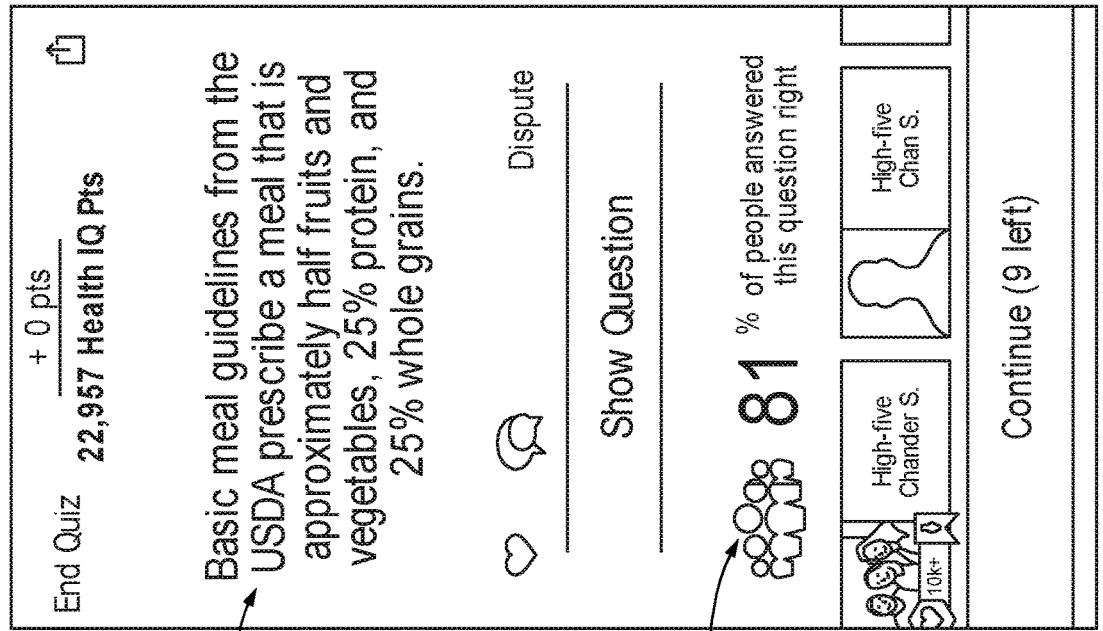
Figure 8C:
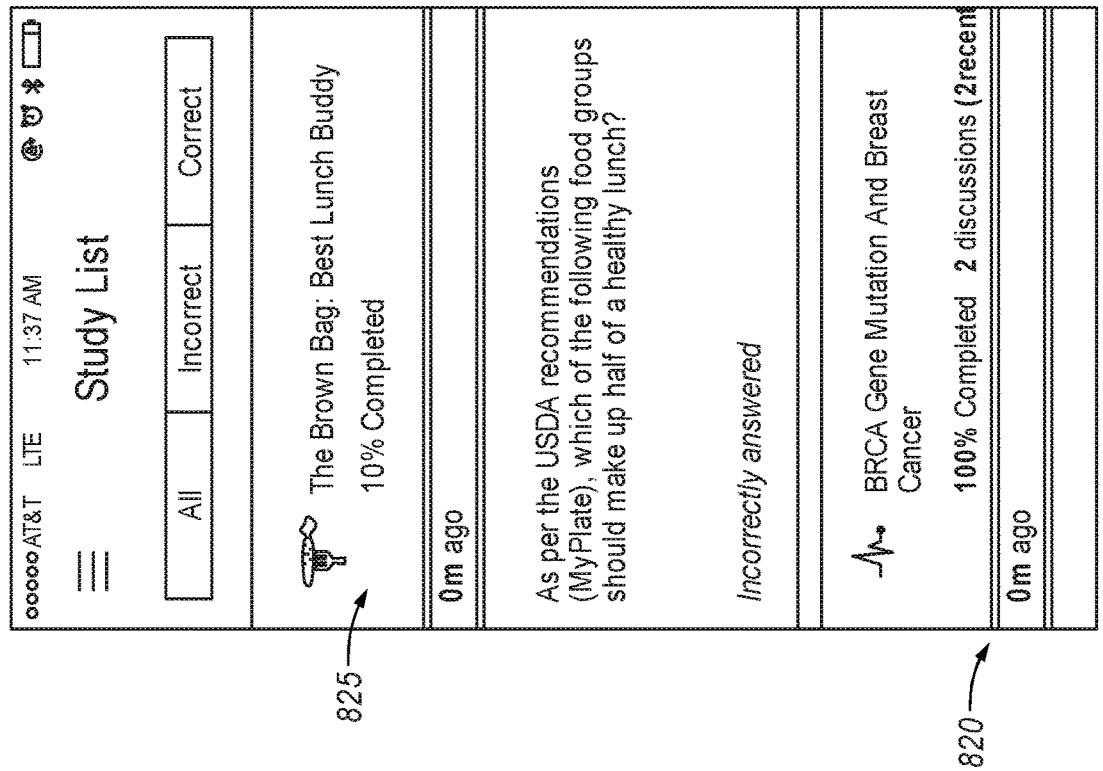

FIG. 8C illustrates a panel 820 that provides feedback 825 to the user as to the correctness of the answer, as well as supplemental information regarding the correct answer and/or assertion underlying the question. In FIG. 8D, once the user provides the answer, the user can be provided an additional panel 830, displaying the underlying assertion 832 behind the question. Other information, such as the percentage of individuals who answer the question correctly can be displayed to the user. This feature 834 can also reflect the difficulty level of the question.

Figure 8F:
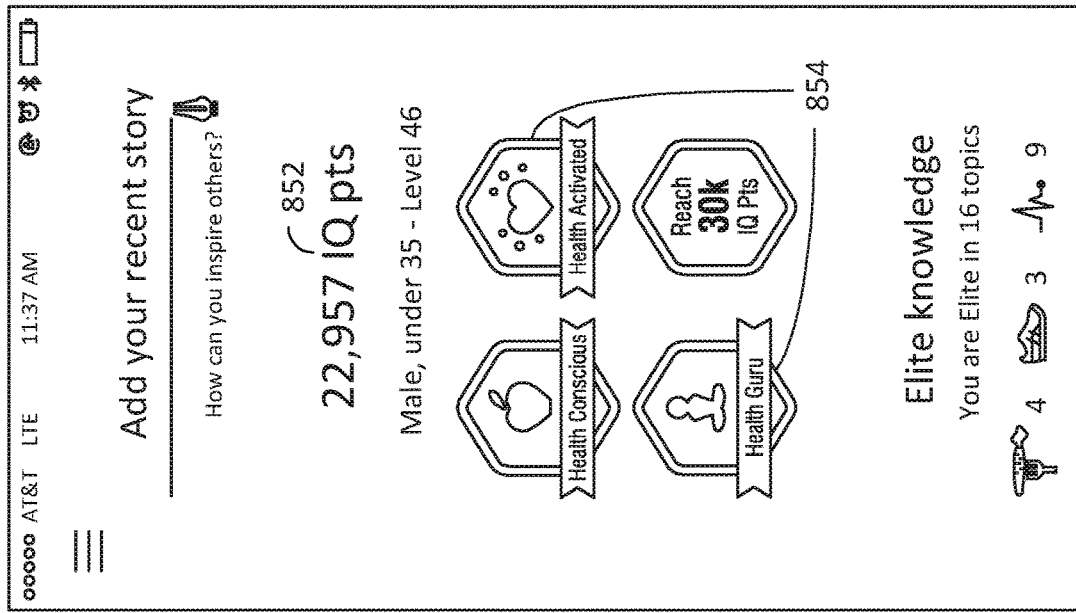
Figure 8E:
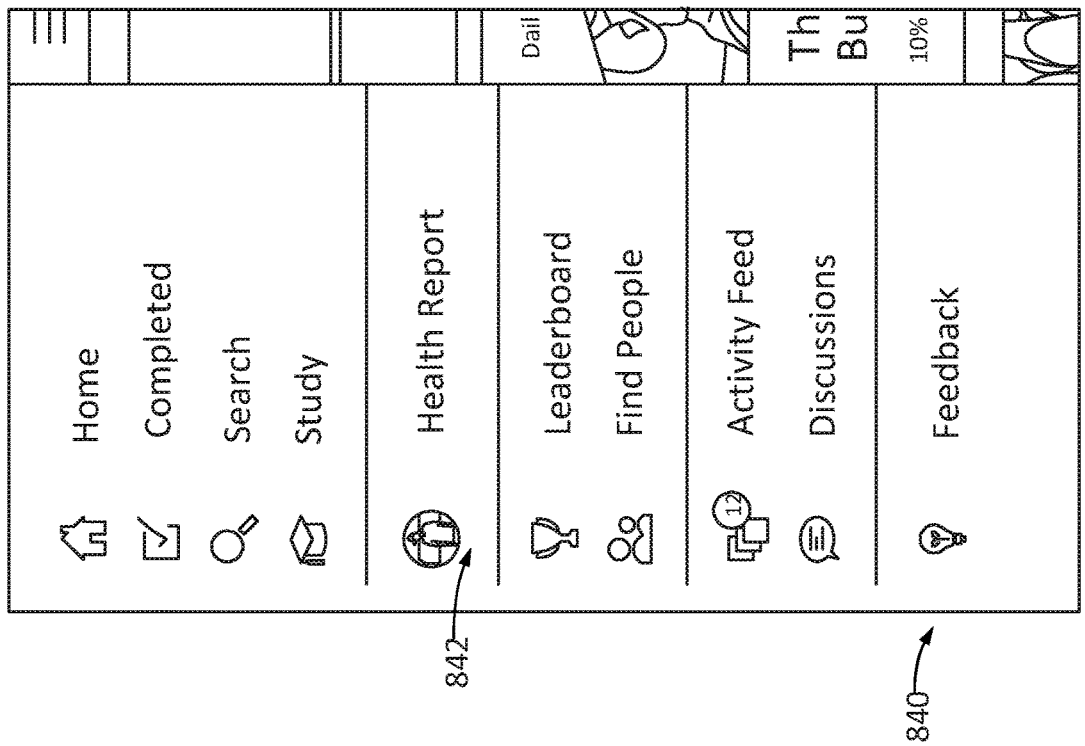

FIG. 8E illustrates a panel 840 on which a menu of options is provided. The user can select from the menu of options. As shown, the functionality provided includes gaming (e.g., leader board) and community interaction (e.g., discussions), in a gaming and social environment such as described with an example of FIG. 1. Additionally, the menu of options can include a health report feature 842 that can display, for example, recommendations as determined from an example of FIG. 7.

FIG. 8F illustrates a panel 850 that provides a gaming summary for the user, displaying the user's overall score 852, as well as badges are honors marking 854 achievements in the number of questions the user answered etc.

Figure 8H:
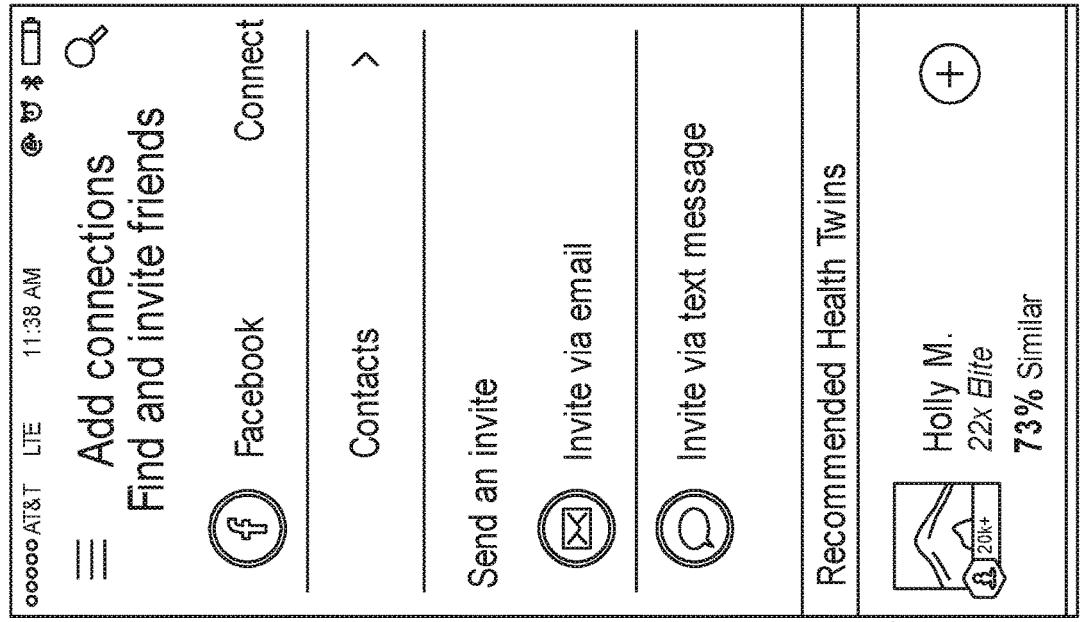
Figure 8G:
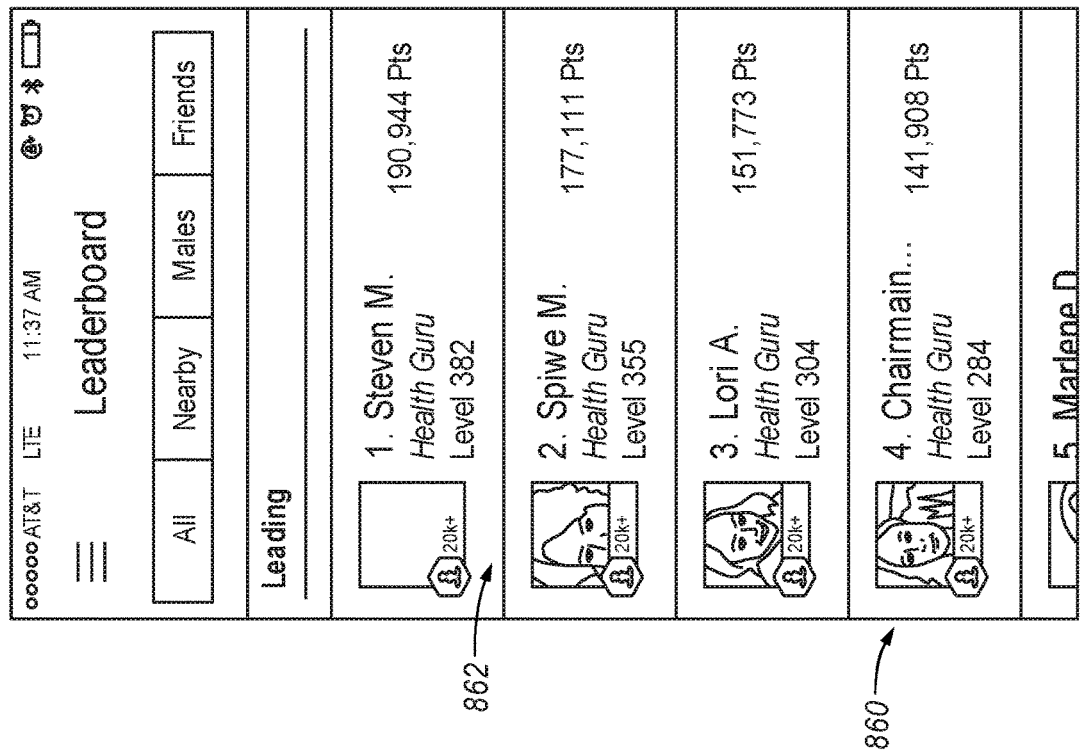

FIG. 8G illustrates a panel 860 on which a leaderboard 862 is provided. The leaderboard can be topic specific and/or categorized by user level.

FIG. 8H illustrates the panel 870 for enabling social interaction, gaming and knowledge base forums through a system such as described with an example of FIG. 1. Among other social interaction functions, one or more knowledge base "twins" can be identified to the user. The twins can correspond to an individual who closely shares one or more of (i) knowledge profile about health, or certain topics of health with the user, and/or (ii) similar or same health outcome values or determinations. As an addition or variation, the twin can also include similar demographic profile, such as having the same gender, age and/or race. Identify twins can be shown to each other as a mechanism for building social interaction and shared experiences, particularly as to distributing health-based knowledge, information and services.

Computer System

One or more embodiments described herein provide that methods, techniques and actions performed by a computing device are performed programmatically, or as a computer-implemented method. Programmatically means through the use of code, or computer-executable instructions. A programmatically performed step may or may not be automatic.

One or more embodiments described herein may be implemented using programmatic modules or components. A programmatic module or component may include a program, a subroutine, a portion of a program, or a software or a hardware component capable of performing one or more stated tasks or functions. As used herein, a module or component can exist on a hardware component independently of other modules or components. Alternatively, a module or component can be a shared element or process of other modules, programs or machines.

Furthermore, one or more embodiments described herein may be implemented through instructions that are executable by one or more processors. These instructions may be carried on a computer-readable medium. Machines shown or described with figures below provide examples of processing resources and computer-readable mediums on which instructions for implementing embodiments of the invention can be carried and/or executed. In particular, the numerous machines shown with embodiments of the invention include processor(s) and various forms of memory for holding data and instructions. Examples of computer-readable mediums include permanent memory storage devices, such as hard drives on personal computers or servers. Other examples of computer storage mediums include portable storage units, such as CD or DVD units, flash or solid state memory (such as carried on many cell phones and consumer electronic devices) and magnetic memory. Computers, terminals, network enabled devices (e.g., mobile devices such as cell phones) are all examples of machines and devices that utilize processors, memory, and instructions stored on computer-readable mediums. Additionally, embodiments may be implemented in the form of computer-programs, or a computer usable carrier medium capable of carrying such a program.

Figure 9:
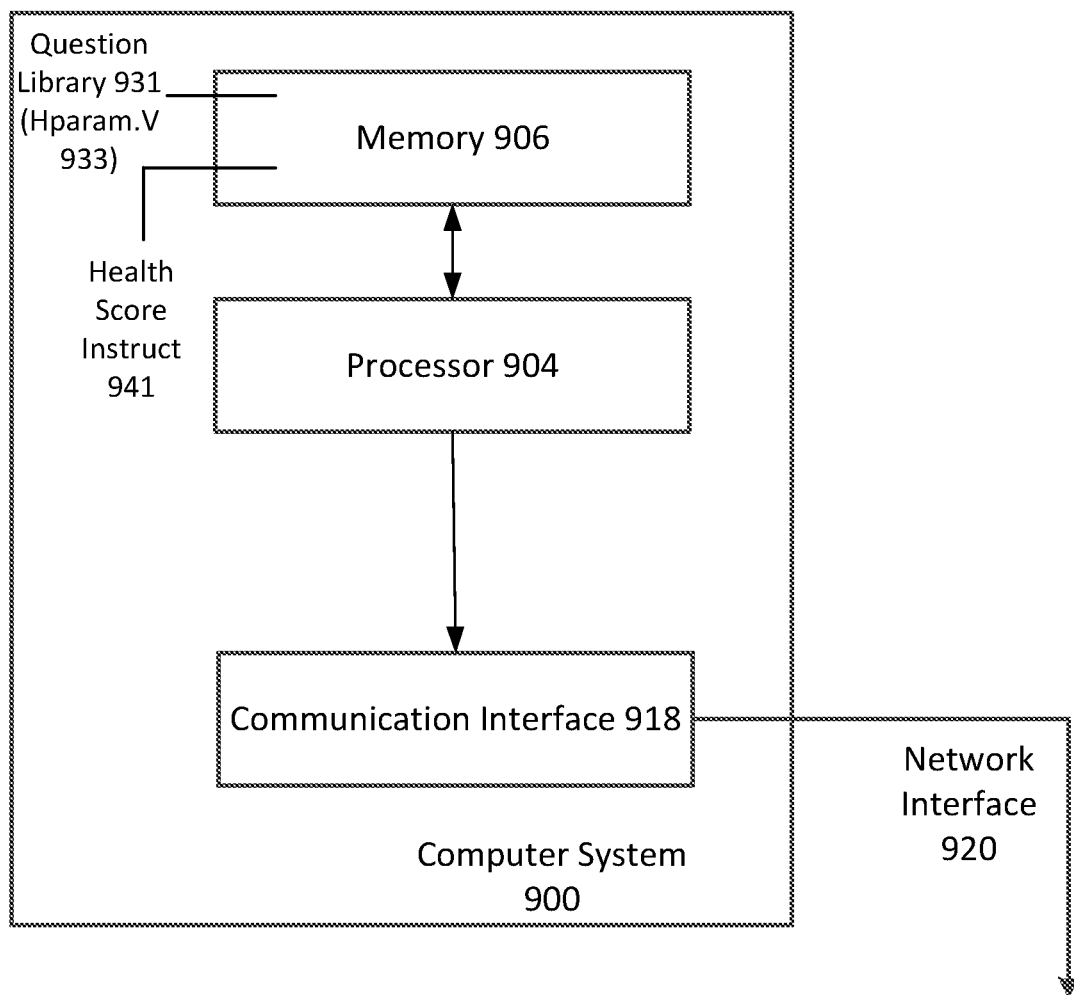
FIG. 9 is a block diagram that illustrates a computer system upon which embodiments described herein may be implemented.

FIG. 9 is a block diagram that illustrates a computer system upon which embodiments described herein may be implemented. For example, in the context of FIG. 1, FIG. 2, FIG. 6B and FIG. 7B, a network service or system can be implemented using one or more computer systems such as described by FIG. 9. Still further, methods such as described with FIG. 4, FIG. 5, FIG. 6A and FIG. 7A can be implemented using a computer system such as described with an example of FIG. 9.

In an embodiment, computer system 900 includes processor 904, memory 906 (including non-transitory memory), storage device, and communication interface 918. Computer system 900 includes at least one processor 904 for processing information. Computer system 900 also includes a memory 906, such as a random access memory (RAM) or other dynamic storage device, for storing information and instructions to be executed by processor 904. The memory 906 also may be used for storing temporary variables or other intermediate information during execution of instructions to be executed by processor 904. Computer system 900 may also include a read only memory (ROM) or other static storage device for storing static information and instructions for processor 904. The communication interface 918 may enable the computer system 900 to communicate with one or more networks through use of the network link 920 (wireless or wireline).

In one implementation, memory 906 may store instructions for implementing functionality such as described with example systems or sub-systems of FIG. 1, FIG. 2, FIG. 6B or FIG. 7B, or implemented through example methods such as described with FIG. 4, FIG. 5, FIG. 6A or FIG. 7A. Likewise, the processor 904 may execute the instructions in providing functionality as described with example systems or sub-systems of FIG. 1, FIG. 2, FIG. 6B or FIG. 7B, or performing operations as described with example methods of FIG. 4, FIG. 5, FIG. 6A or FIG. 7A.

Embodiments described herein are related to the use of computer system 900 for implementing functionality as described herein. The memory 906, for example, can store a question library 931 (see, e.g., also question library 152 of FIG. 1), including values for health correlative parameters 933 (see e.g., also health correlative parameters 151 of FIG. 1) of the some questions. The memory 906 can also store instructions 941 for determining a health score, in order to determine one or more correlative health parameters for a user, in connection with the user's participation of responding to questions in an interactive community or game environment.

According to one embodiment, functionality such as described herein can be performed by computer system 900 in response to processor 904 executing one or more sequences of one or more instructions contained in the memory 906. Such instructions may be read into memory 906 from another machine-readable medium, such as through a non-transitory storage device. Execution of the sequences of instructions contained in memory 906 causes processor 904 to perform the process steps described herein. In alternative embodiments, hard-wired circuitry may be used in place of or in combination with software instructions to implement embodiments described herein. Thus, embodiments described are not limited to any specific combination of hardware circuitry and software.

Although illustrative embodiments have been described in detail herein with reference to the accompanying drawings, variations to specific embodiments and details are encompassed by this disclosure. It is intended that the scope of embodiments described herein be defined by claims and their equivalents. Furthermore, it is contemplated that a particular feature described, either individually or as part of an embodiment, can be combined with other individually described features, or parts of other embodiments. Thus, absence of describing combinations should not preclude the inventor(s) from claiming rights to such combinations.

What is claimed is:

1. A computing system implementing health service, the computing system comprising:
   a network communication interface to communicate, over one or more wireless networks, with computing devices of users of the health service;
   one or more processors;
   a memory storing instructions that, when executed by the one or more processors, cause the one or more processors to:
   execute a correlation model to determine a correlation value for each respective health assertion in a collection of health assertions based on (i) answers to the respective health assertion provided by individuals in a control group, and (ii) known health outcomes of each individual in the control group, wherein the correlation value for each respective health assertion in the collection corresponds to a set of health correlations between knowledge associated with the respective health assertion and the known health outcomes of the individuals in the control group;
   receive, over the one or more wireless networks, activity data from a wearable activity monitoring device of a user of the health service, the activity data indicating at least one of (i) a distance traveled during an exercise routine, (ii) a type of exercise routine performed by the user, (iii) a duration of an exercise routine, or (iv) biometric data of the user from one or more sensors of the wearable activity monitoring device;
   generate, over the one or more wireless networks, a health trivia session to be presented on a computing device of the user, the health trivia session comprising a set of health assertions from the collection of health assertions;
   receive, over the one or more wireless networks, a corresponding set of responses to the set of health assertions from the computing device of the user;
   for each response in the corresponding set of responses, determine a correctness for the response, the correctness indicating whether the user answered a corresponding health assertion correctly or incorrectly;
   based on (i) the correctness of each response in the corresponding set of responses, (ii) the correlation value of each health assertion in the set of health assertions provided during the trivia session, and (iii) the activity data of the user, generate a health profile for the user;
   based on the health profile of the user, determine whether the user qualifies for one or more health service benefits; and
   in response to determining that the user qualifies for one or more health service benefits, generate, over the one or more wireless networks, a service customer interface to be displayed on the computing device of the user, the service customer interface enabling the user to redeem or purchase a health service product using the one or more health service benefits.

2. The computing system of claim 1, wherein the executed instructions further cause the computing system to:
transmit, over the one or more wireless, a set of queries to the computing device of the user, the set of queries being transmitted to determine an age, a gender, a weight, and a height of the user;
wherein the executed instructions cause the computing system to further generate the health profile of the user based on the age, the gender, the weight, and the height of the user.

3. The computing system of claim 1, wherein the executed instructions further cause the computing system to:
receive, over the one or more wireless networks, health data indicating actual health outcomes of additional users of the health service; and
include the additional users into the control group.

4. The computing system of claim 3, wherein the executed instructions cause the computing system to include the additional users in the control group by:
determining previous responses to a subset of the collection of health assertions provided by each of the additional users; and
based on the previous responses and the health data of the additional users, executing the correlation model to calibrate the correlation value of each health assertion in the subset of the collection of health assertions.

5. The computing system of claim 1, wherein the correlation value for each respective health assertion in a collection of health assertions maps the respective health assertion to at least one of a plurality of possible health outcomes.

6. The computing system of claim 5, wherein the plurality of possible health outcomes correspond to a risk of at least one of cancer, heart disease, diabetes, hypertension, or obesity.

7. The computing system of claim 1, wherein the one or more health service benefits comprise at least one of a premium or a discount for the user for the health service product.

8. The computing system of claim 7, wherein the health service product comprises a life insurance product.

9. A non-transitory computer readable medium storing instructions that, when executed by one or more processors of a computing system, cause the computing system to:
communicate, over one or more wireless networks, with computing devices of users of a health service;
execute a correlation model to determine a correlation value for each respective health assertion in a collection of health assertions based on (i) answers to the respective health assertion provided by individuals in a control group, and (ii) known health outcomes of each individual in the control group, wherein the correlation value for each respective health assertion in the collection corresponds to a set of health correlations between knowledge associated with the respective health assertion and the known health outcomes of the individuals in the control group;
receive, over the one or more wireless networks, activity data from a wearable activity monitoring device of a user of the health service, the activity data indicating at least one of (i) a distance traveled during an exercise routine, (ii) a type of exercise routine performed by the user, (iii) a duration of an exercise routine, or (iv) biometric data of the user from one or more sensors of the wearable activity monitoring device;
generate, over the one or more wireless networks, a health trivia session to be presented on a computing device of the user, the health trivia session comprising a set of health assertions from the collection of health assertions;
receive, over the one or more wireless networks, a corresponding set of responses to the set of health assertions from the computing device of the user;
for each response in the corresponding set of responses, determine a correctness for the response, the correctness indicating whether the user answered a corresponding health assertion correctly or incorrectly;
based on (i) the correctness of each response in the corresponding set of responses, (ii) the correlation value of each health assertion in the set of health assertions provided during the trivia session, and (iii) the activity data of the user, generate a health profile for the user;
based on the health profile of the user, determine whether the user qualifies for one or more health service benefits; and
in response to determining that the user qualifies for one or more health service benefits, generate, over the one or more wireless networks, a service customer interface to be displayed on the computing device of the user, the service customer interface enabling the user to redeem or purchase a health service product using the one or more health service benefits.

10. The non-transitory computer readable medium of claim 9, wherein the executed instructions further cause the computing system to:
transmit, over the one or more wireless, a set of queries to the computing device of the user, the set of queries being transmitted to determine an age, a gender, a weight, and a height of the user;
wherein the executed instructions cause the computing system to further generate the health profile of the user based on the age, the gender, the weight, and the height of the user.

11. The non-transitory computer readable medium of claim 9, wherein the executed instructions further cause the computing system to:
receive, over the one or more wireless networks, health data indicating actual health outcomes of additional users of the health service; and
include the additional users into the control group.

12. The computing system of claim 11, wherein the executed instructions cause the computing system to include the additional users in the control group by:
determining previous responses to a subset of the collection of health assertions provided by each of the additional users; and
based on the previous responses and the health data of the additional users, executing the correlation model to calibrate the correlation value of each health assertion in the subset of the collection of health assertions.

13. The non-transitory computer readable medium of claim 9, wherein the correlation value for each respective health assertion in a collection of health assertions maps the respective health assertion to at least one of a plurality of possible health outcomes.

14. The non-transitory computer readable medium of claim 13, wherein the plurality of possible health outcomes correspond to a risk of at least one of cancer, heart disease, diabetes, hypertension, or obesity.

15. The non-transitory computer readable medium of claim 9, wherein the one or more health service benefits comprise at least one of a premium or a discount for the user for the health service product.

16. The non-transitory computer readable medium of claim 15, wherein the health service product comprises a life insurance product.

17. A computer-implemented method of implementing a health service, the method being performed by one or more processors of a computing system and comprising:
communicating, over one or more wireless networks, with computing devices of users of the health service;
executing a correlation model to determine a correlation value for each respective health assertion in a collection of health assertions based on (i) answers to the respective health assertion provided by individuals in a control group, and (ii) known health outcomes of each individual in the control group, wherein the correlation value for each respective health assertion in the collection corresponds to a set of health correlations between knowledge associated with the respective health assertion and the known health outcomes of the individuals in the control group;
receiving, over the one or more wireless networks, activity data from a wearable activity monitoring device of a user of the health service, the activity data indicating at least one of (i) a distance traveled during an exercise routine, (ii) a type of exercise routine performed by the user, (iii) a duration of an exercise routine, or (iv) biometric data of the user from one or more sensors of the wearable activity monitoring device;
generating, over the one or more wireless networks, a health trivia session to be presented on a computing device of the user, the health trivia session comprising a set of health assertions from the collection of health assertions;
receiving, over the one or more wireless networks, a corresponding set of responses to the set of health assertions from the computing device of the user;
for each response in the corresponding set of responses, determining a correctness for the response, the correctness indicating whether the user answered a corresponding health assertion correctly or incorrectly;
based on (i) the correctness of each response in the corresponding set of responses, (ii) the correlation value of each health assertion in the set of health assertions provided during the trivia session, and (iii) the activity data of the user, generating a health profile for the user;
based on the health profile of the user, determining whether the user qualifies for one or more health service benefits; and
in response to determining that the user qualifies for one or more health service benefits, generating, over the one or more wireless networks, a service customer interface to be displayed on the computing device of the user, the service customer interface enabling the user to redeem or purchase a health service product using the one or more health service benefits.

18. The method of claim 17, further comprising:
transmitting, over the one or more wireless, a set of queries to the computing device of the user, the set of queries to being transmitted to determine an age, a gender, a weight, and a height of the user;
wherein the computing system further generates the health profile of the user based on the age, the gender, the weight, and the height of the user.

19. The computing system of claim 17, further comprising:
receiving, over the one or more wireless networks, health data indicating actual health outcomes of additional users of the health service; and
including the additional users into the control group.

20. The computing system of claim 19, wherein the computing system includes the additional users in the control group by:
determining previous responses to a subset of the collection of health assertions provided by each of the additional users; and
based on the previous responses and the health data of the additional users, executing the correlation model to calibrate the correlation value of each health assertion in the subset of the collection of health assertions.

* * * * *